(12) United States Patent
Baker et al.

(10) Patent No.: US 11,135,374 B2
(45) Date of Patent: Oct. 5, 2021

(54) MEDICAMENT DELIVERY AND SIMULATION SYSTEM WITH A REMOVABLE DISPOSABLE CONTAINER FOR MEDICAMENT DELIVERY AND TRAINING

(71) Applicant: NOBLE INTERNATIONAL, INC., Orlando, FL (US)

(72) Inventors: Jeff Baker, Orlando, FL (US); Shishuang Hou, Ningbo (CN); Paul van der Pol, Winter Garden, FL (US)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 81 days.

(21) Appl. No.: 16/369,030

(22) Filed: Mar. 29, 2019

(65) Prior Publication Data
US 2019/0290858 A1 Sep. 26, 2019

Related U.S. Application Data

(63) Continuation of application No. PCT/US2014/030326, filed on Mar. 17, 2014, which
(Continued)

(51) Int. Cl.
*A61M 5/315* (2006.01)
*G09B 23/28* (2006.01)
(Continued)

(52) U.S. Cl.
CPC ...... *A61M 5/31566* (2013.01); *A61M 5/1456* (2013.01); *A61M 5/14212* (2013.01);
(Continued)

(58) Field of Classification Search
CPC ............ A61M 5/31566; A61M 5/1456; A61M 5/14212; A61M 2005/14256; A61M 5/3158; A61M 5/3221
See application file for complete search history.

(56) References Cited

U.S. PATENT DOCUMENTS 5,578,014 A * 11/1996 Erez .......................... A61F 7/10
604/192
6,203,529 B1 * 3/2001 Gabriel ............... A61M 5/3202
604/192
(Continued)

*Primary Examiner* — Bradley J Osinski
(74) *Attorney, Agent, or Firm* — Timothy H. Van Dyke; Wolter Van Dyke Davis, PLLC

(57) ABSTRACT

Embodiments of the invention include a medicament device configured to provide stepwise instructions for using the device to a user in a particular sequence is provided. The device includes a device housing configured to receive a container, the housing including a control interface, the control interface including at least one responsive member reactive to a user input, an actuation mechanism configured to interact with the container, a signal output component associated with the device housing, and circuitry associated with the device housing configured to control a provision of the stepwise instructions to the user in the particular sequence. The container includes a first housing for containing a medicament, a second housing, and an injection member, wherein the first and second housings are movable relative to one another. The container further includes an injection member which is retractable within the second housing to prevent an unintentional contact with the injection member.

12 Claims, 16 Drawing Sheets

Related U.S. Application Data is a continuation of application No. 14/208,357, filed on Mar. 13, 2014, now Pat. No. 10,245,385, which is a continuation of application No. 14/017,933, filed on Sep. 4, 2013, now abandoned.

(60) Provisional application No. 61/788,033, filed on Mar. 15, 2013.

(51) Int. Cl.
  *A61M 5/145* (2006.01)
  *A61M 5/20* (2006.01)
  *A61M 5/142* (2006.01)
  *A61M 5/19* (2006.01)
  *A61M 5/32* (2006.01)

(52) U.S. Cl.
  CPC ............... *A61M 5/19* (2013.01); *A61M 5/20* (2013.01); *A61M 5/2033* (2013.01); *A61M 5/31573* (2013.01); *G09B 23/285* (2013.01); *A61M 5/1454* (2013.01); *A61M 5/3158* (2013.01); *A61M 5/3221* (2013.01); *A61M 5/3232* (2013.01); *A61M 2005/14256* (2013.01); *A61M 2005/14288* (2013.01); *A61M 2005/14513* (2013.01); *A61M 2005/14533* (2013.01); *A61M 2005/206* (2013.01); *A61M 2205/18* (2013.01); *A61M 2205/3368* (2013.01); *A61M 2205/502* (2013.01); *A61M 2205/58* (2013.01); *A61M 2205/6072* (2013.01)

(56) References Cited

U.S. PATENT DOCUMENTS

| | | | |
|---|---|---|---|
| 6,537,257 B1 * | 3/2003 | Wien | A61M 5/3202 604/198 |
| 6,997,906 B2 | 2/2006 | Langley et al. | |
| 7,704,231 B2 | 4/2010 | Pongpairochana et al. | |
| 7,740,612 B2 | 6/2010 | Hochman | |
| 8,088,096 B2 | 1/2012 | Lauchard et al. | |
| 8,105,283 B2 | 1/2012 | Perriere | |
| 8,303,535 B2 | 11/2012 | Both et al. | |
| 2009/0030366 A1 | 1/2009 | Hochman | |
| 2012/0008811 A1 | 1/2012 | Edwards et al. | |
| 2012/0078224 A1 | 3/2012 | Lerner | |
| 2012/0253314 A1 | 10/2012 | Harish et al. | |

* cited by examiner

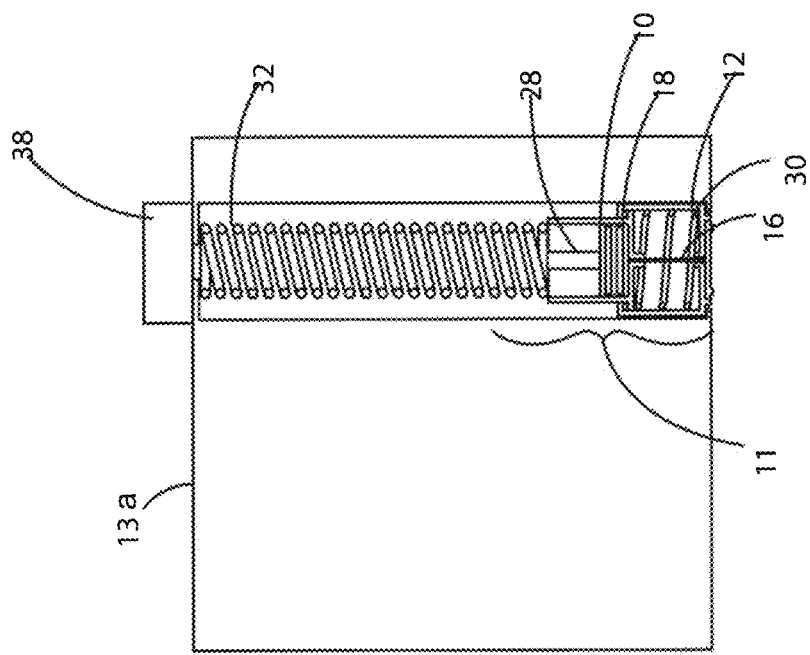
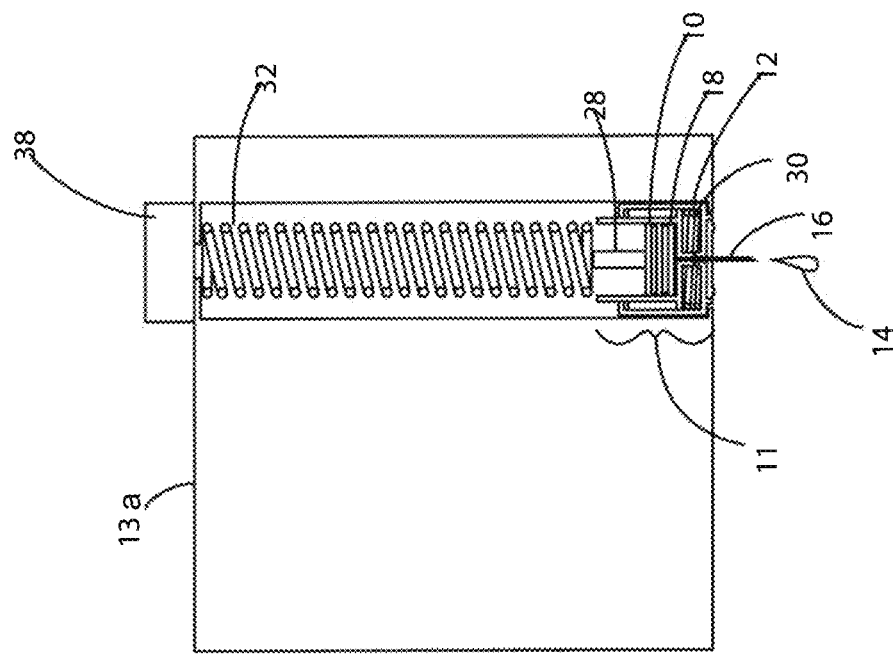

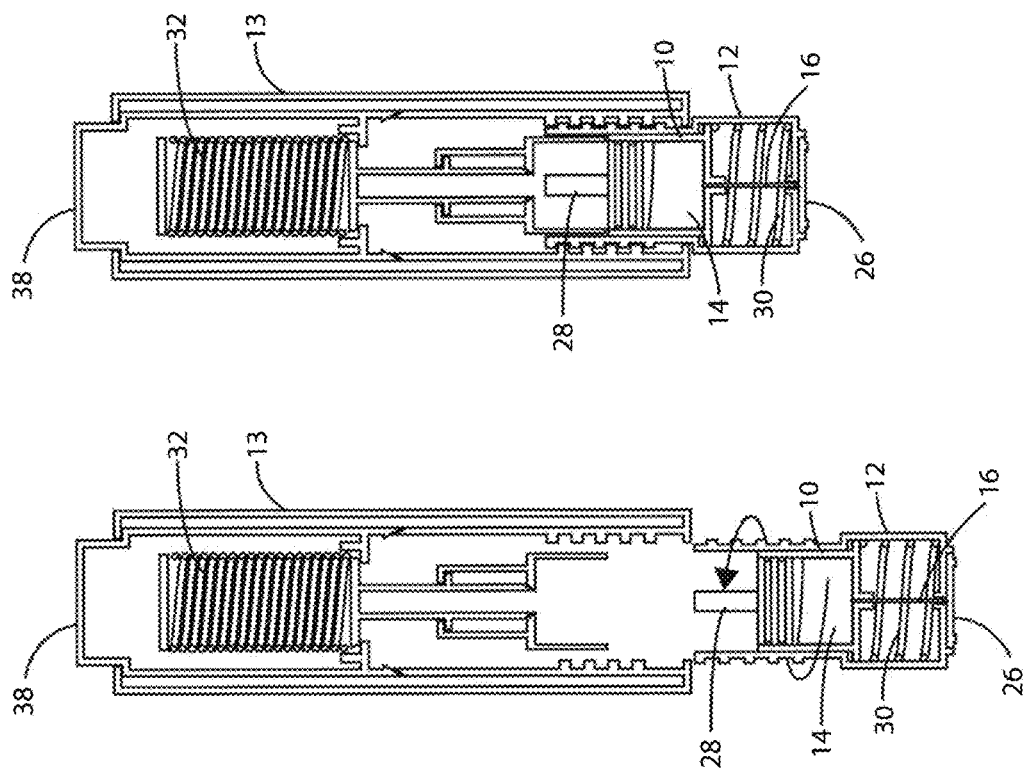
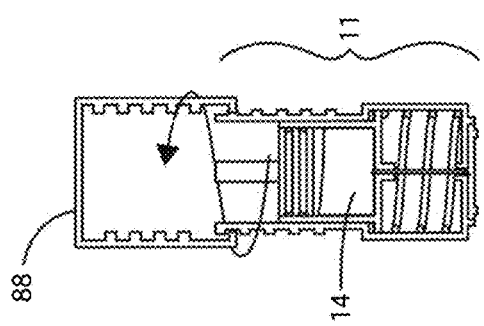
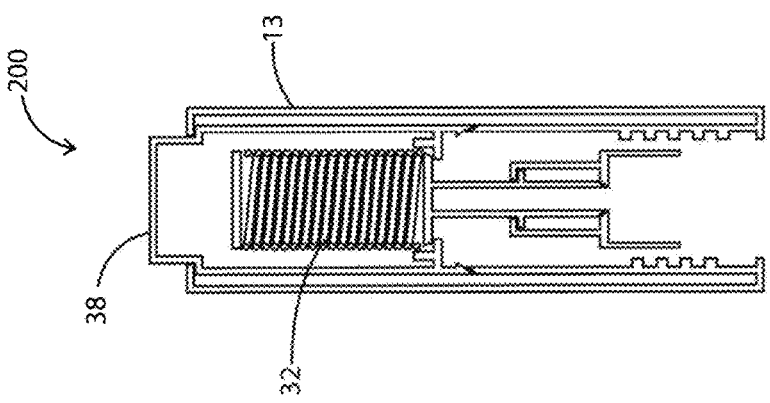

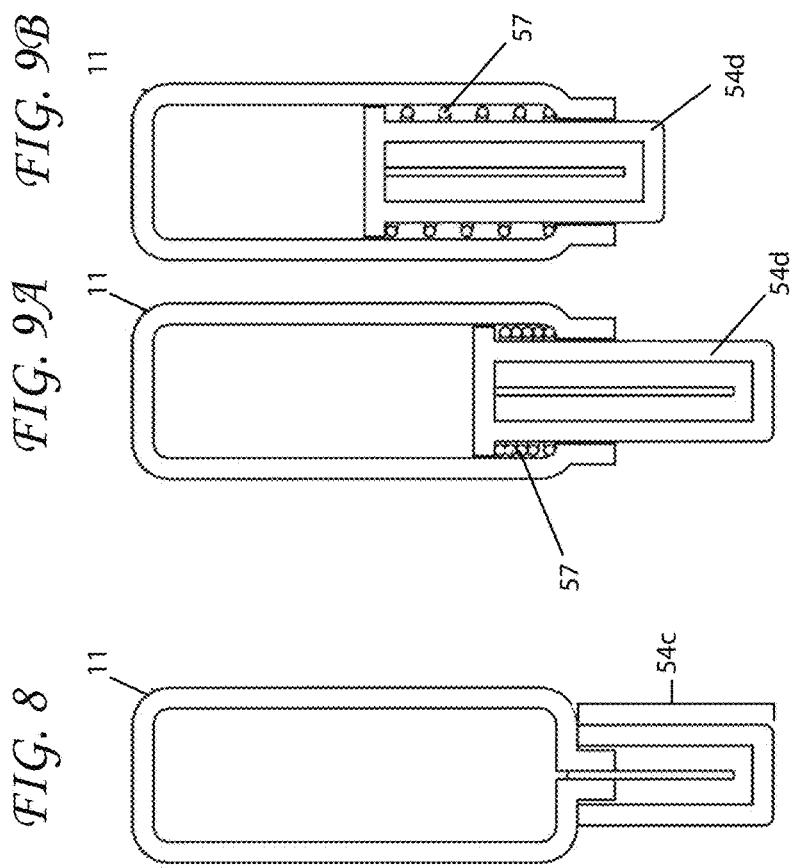

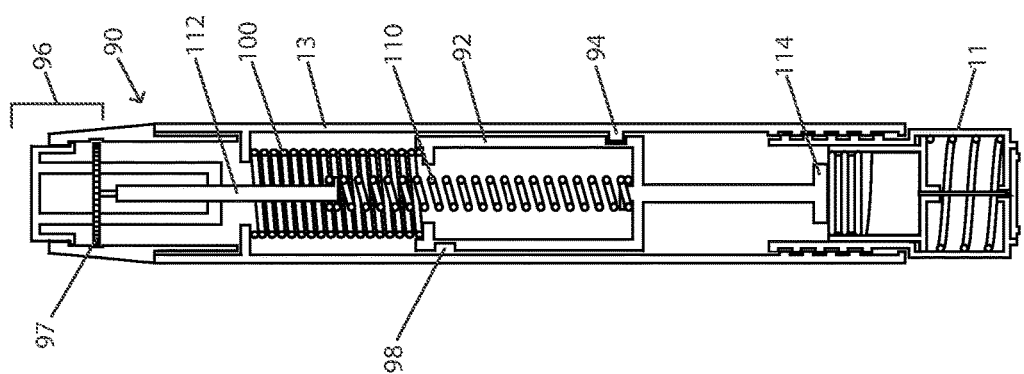
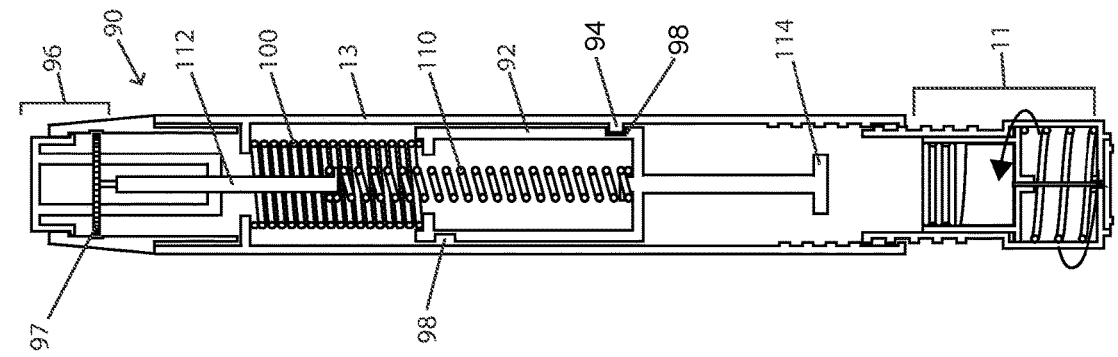
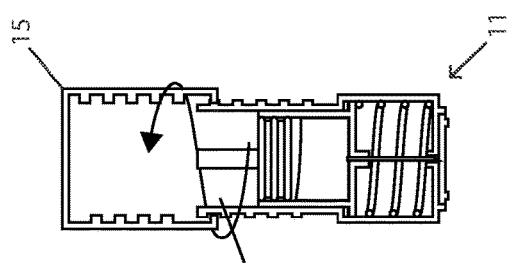
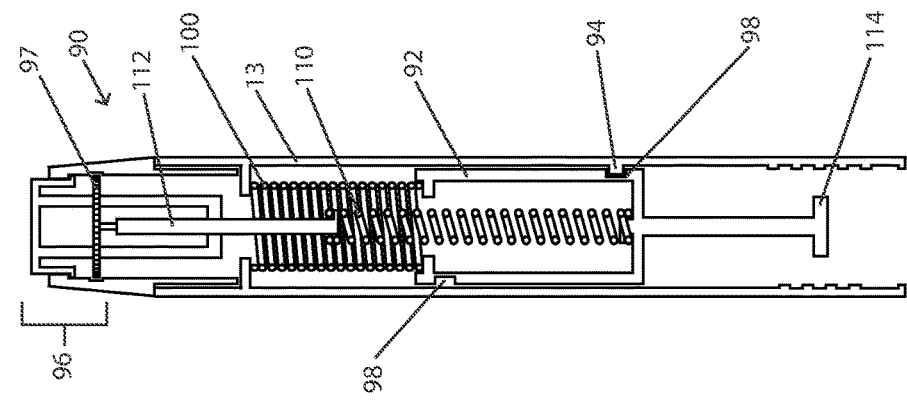

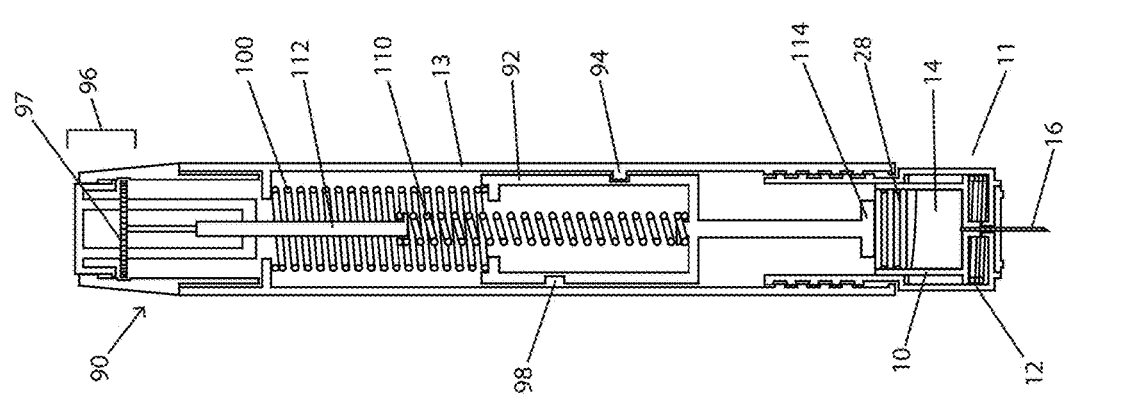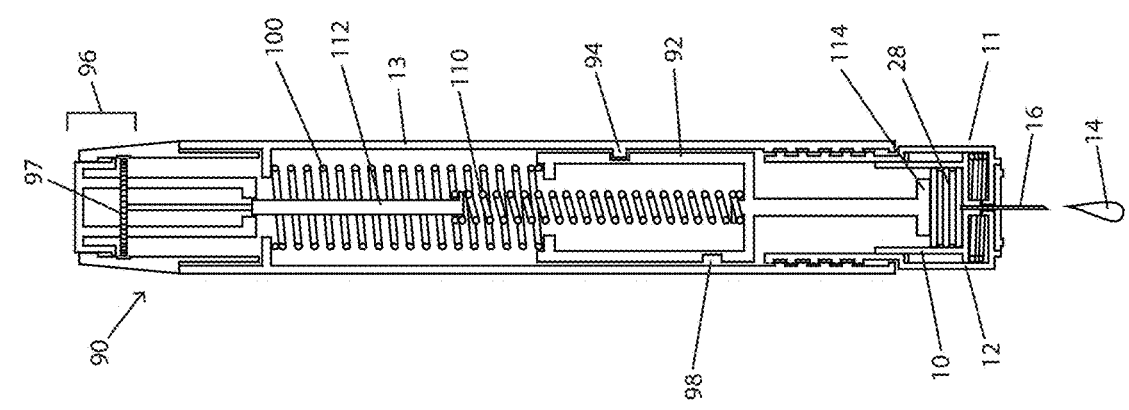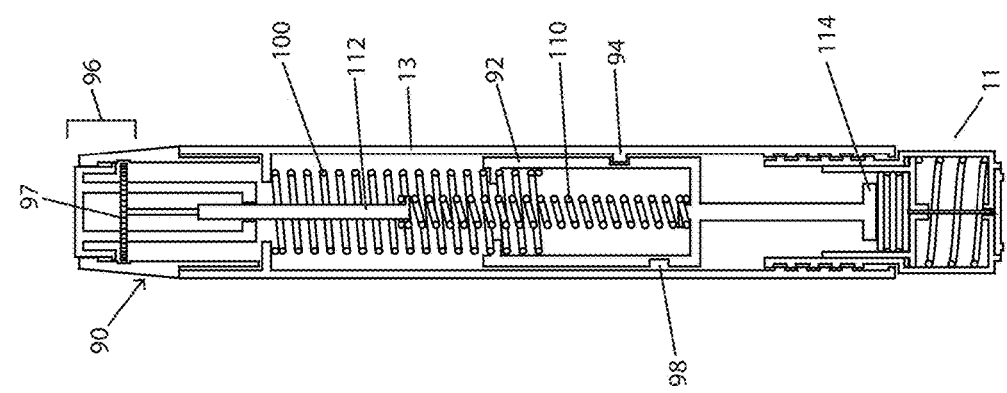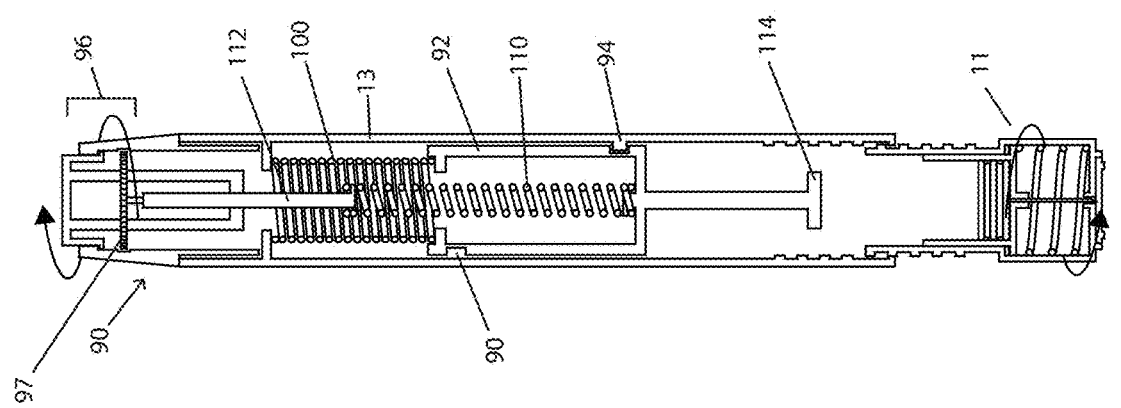

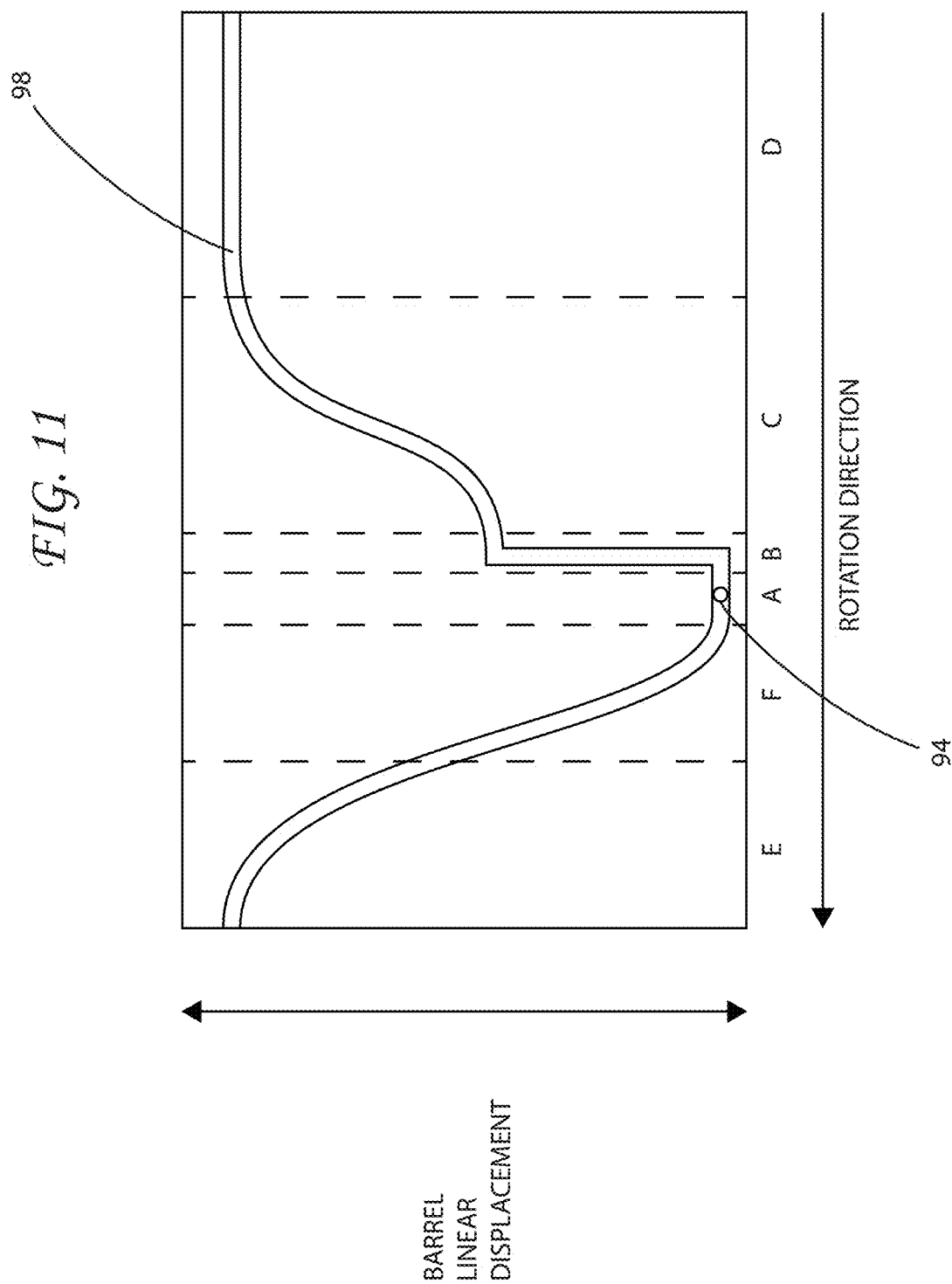

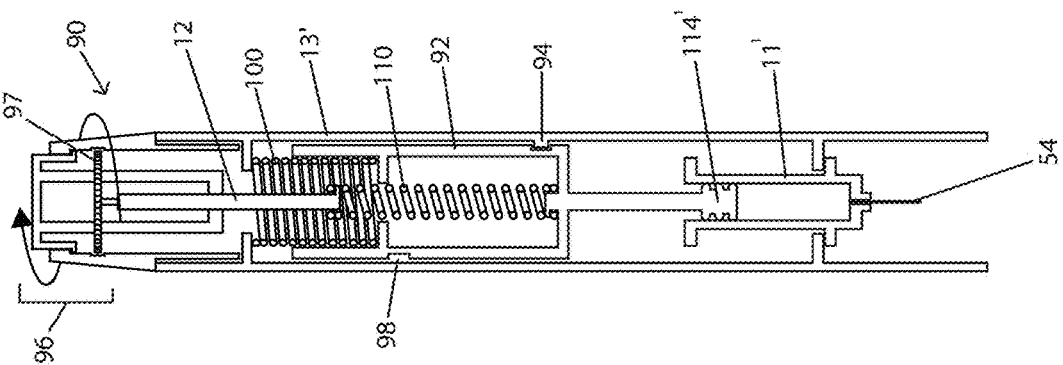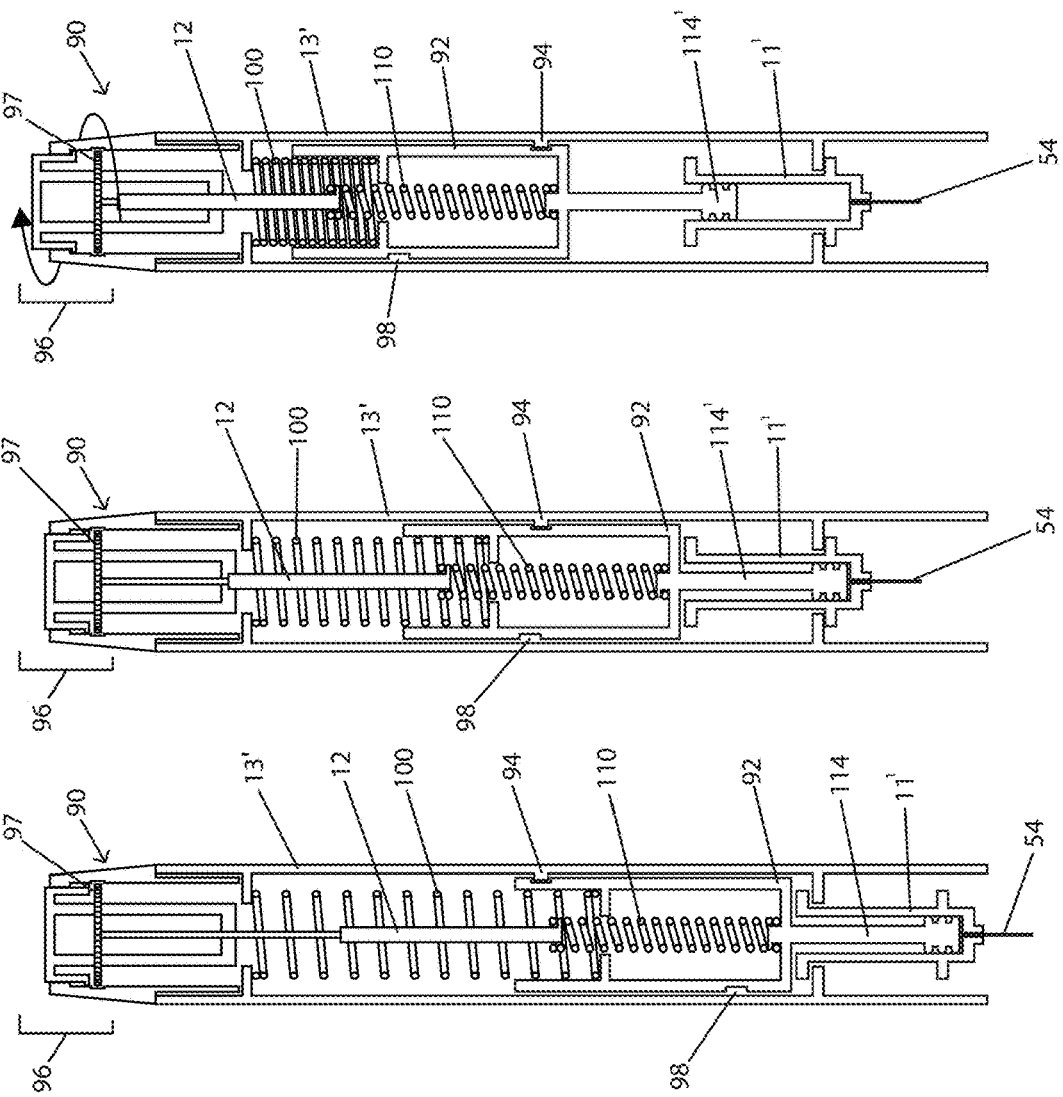

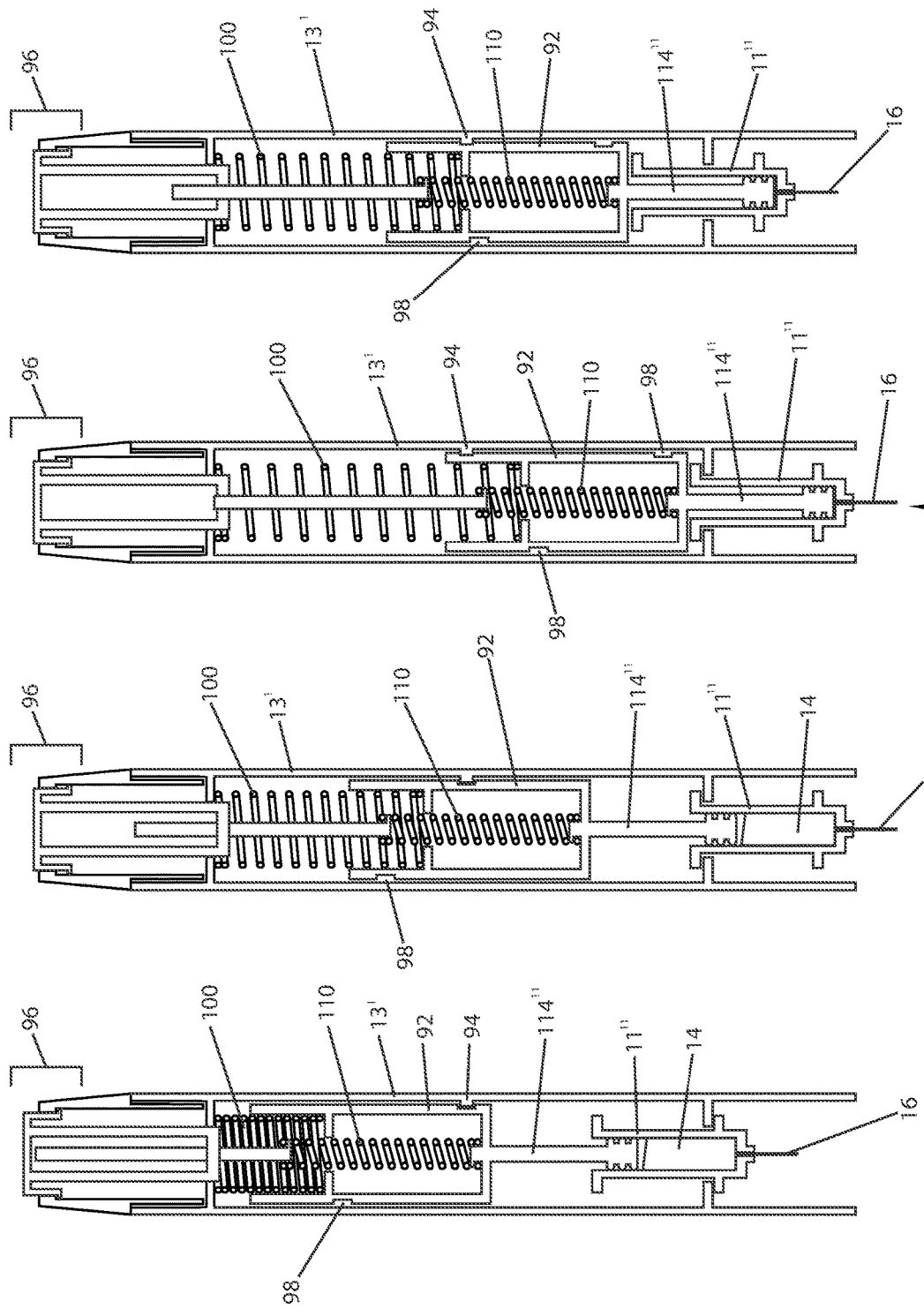

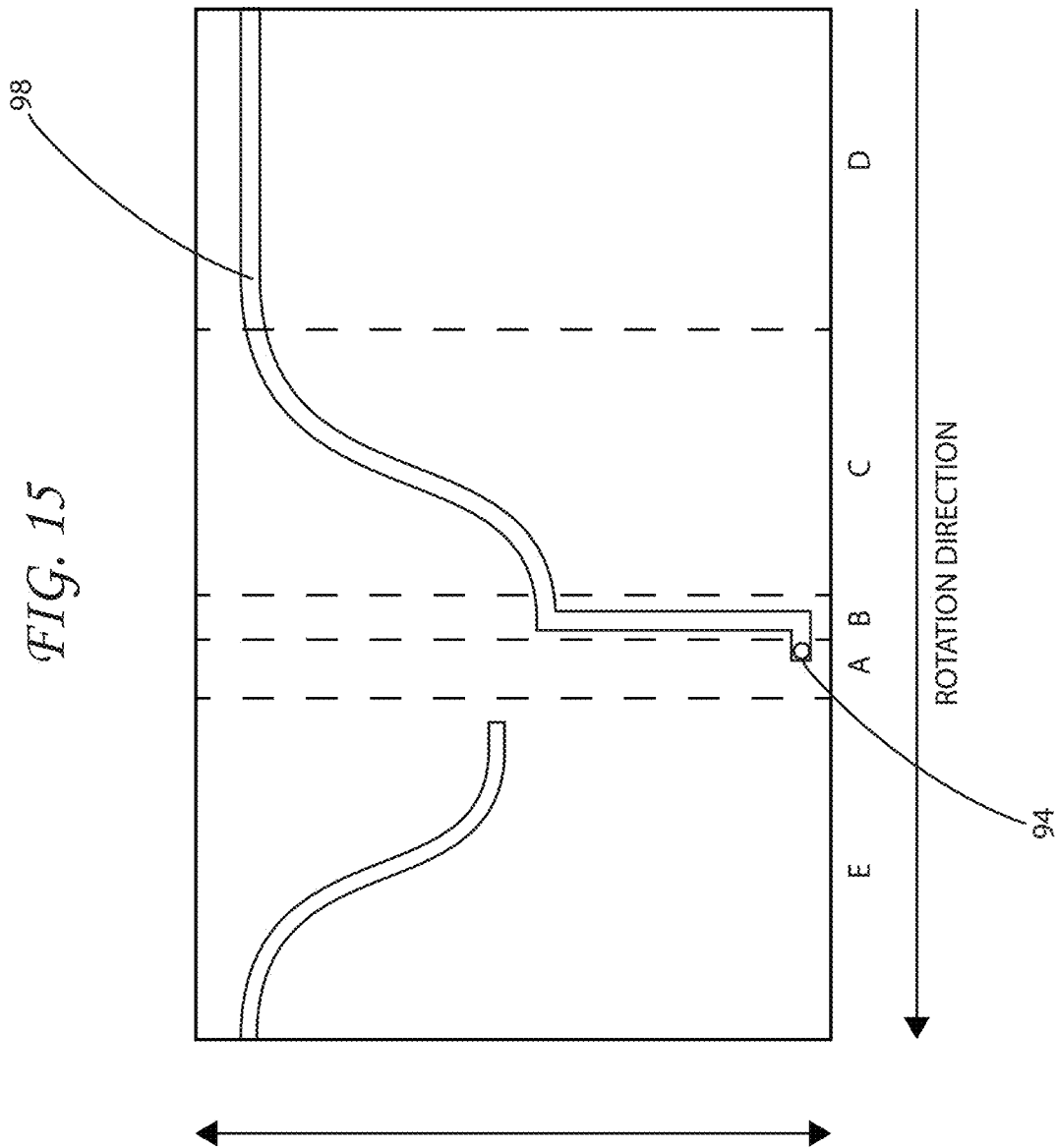

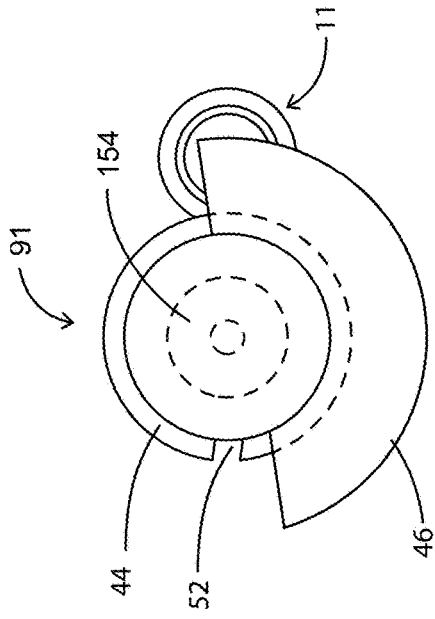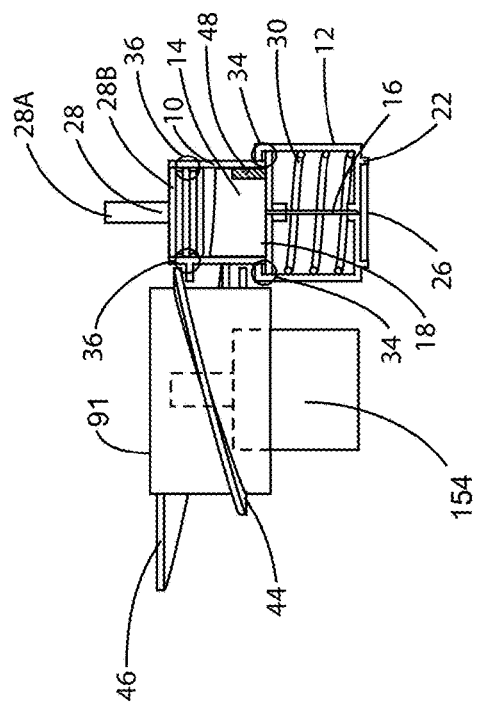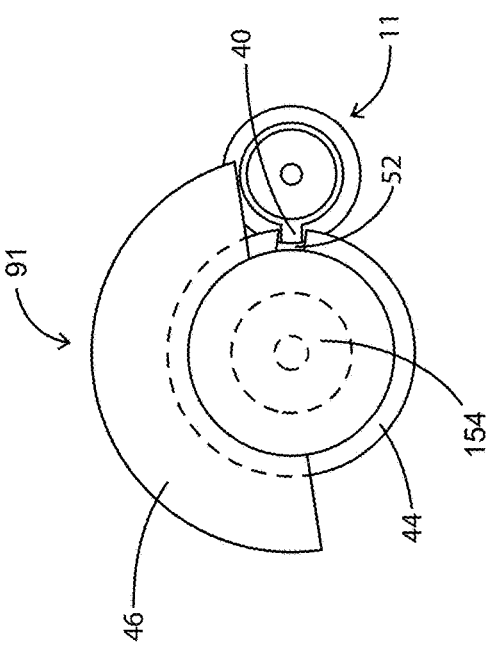

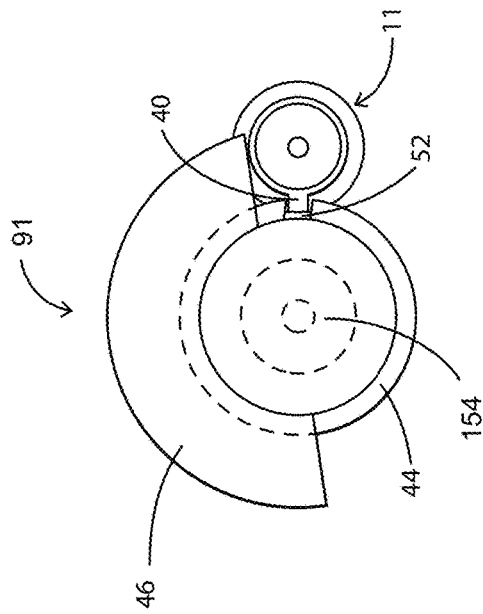
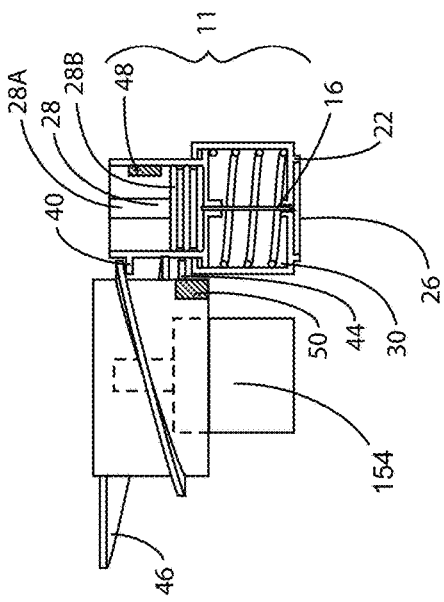
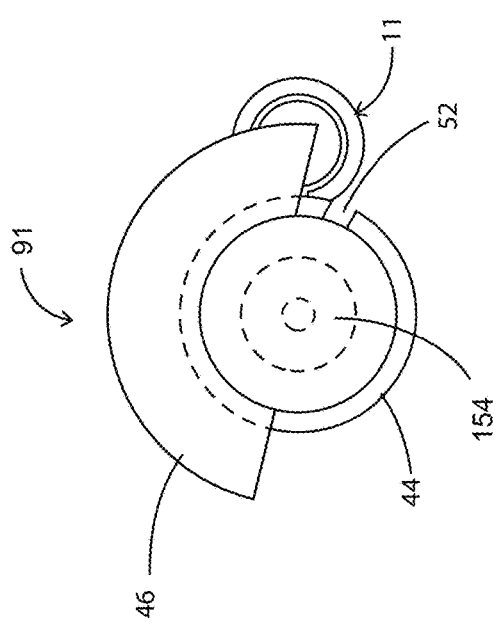
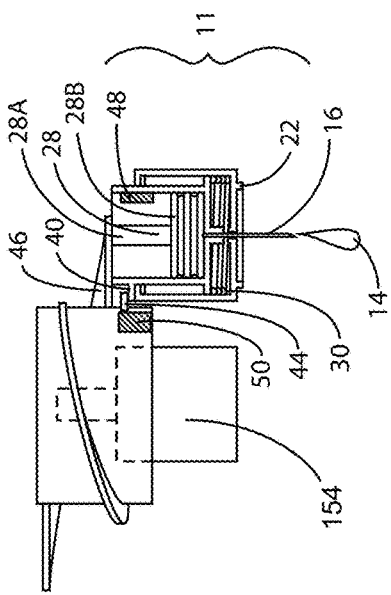

MEDICAMENT DELIVERY AND SIMULATION SYSTEM WITH A REMOVABLE DISPOSABLE CONTAINER FOR MEDICAMENT DELIVERY AND TRAINING

BACKGROUND

Manual disposable syringe based devices have existed since the mid-1800's. These devices were designed for a single purpose of performing a subcutaneous injection through a hollow-bore needle affixed to the syringe device. Syringes are simple mechanical systems with no capability of refined fluid dynamics or ability to integrate advanced digital capabilities. Auto-injection or "pen" devices have recently become increasingly popular for single dose or multi dose, at home self-administration. These auto-injection devices are primarily designed to accomplish two basic objectives: convenience and automation of drug delivery in an outpatient setting. These are typically mechanically spring-loaded devices that advance a plunger or rubber stopper to transfer medication via hollow-bore needle to a patient's tissues. Auto-injection devices lack the ability to regulate whether the medication is actually delivered to the patient or whether it is delivered to a correct location. Most auto-injection devices fail to integrate advanced digital capabilities.

A significant limitation is the inability of auto-injection devices to collect and transfer digital information from the device to other sources. Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. Auto-injection devices are routinely used to provide a means for self-injecting certain medications. The size and operation of these auto-injection devices can often be daunting to a patient, whether they are injecting themselves for the first or they have injected themselves before. These fears and anxieties associated with the currently available self-injection devices, particularly the auto-injection devices, may result in the administration of an incomplete dose of a medicament, failure to administer any portion of the dose of a medicament, or accidentally sticking oneself with the needle of the device, which in some instances could lead to unwanted transmission of diseases if the needle is contaminated.

In some instances, after an auto-injection is complete, the contaminated needle is retracted within the auto-injection device or covered over by a needle guard or sheath and the entire auto-injection device is disposed of. Therefore, most auto-injectors currently available are single use auto-injectors. These single use auto-injectors are costly and economically wasteful. Alternatively, there are injection devices which require a user to re-cap a needle after the injection is complete such that the disposable needle can be removed and discarded. These injection devices carry with them the risk of unwanted sticking of oneself during re-capping of the needle.

An additional concern exists with regard to injection devices, and in particular with regard to auto-injectors, where users with little or no medical knowledge or experience are injecting themselves or injecting others using these devices. Performing a medical treatment or test on oneself or others carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery.

Therefore, there exists a need for an injection device which may be safely and efficiently used by patients without medical experience in preparing and self-injecting medications. Furthermore, a device which closely resembles a medicament delivery device that can be used to simulate an injection for training purposes would be highly beneficial.

SUMMARY

In one embodiment, a training container device configured to provide stepwise instructions for using the device to a user in a particular sequence is provided. The training container device includes a first housing, and a second housing, wherein the first housing is movable relative to the second housing. The training container device further includes an injection simulation member associated with a lower portion of the first housing, wherein when the first housing moves relative to the second housing in a first direction, the injection member ejects from the second housing traversing a first contaminant barrier disposed at a lower portion of the second housing. When the first housing moves relative to the second housing in a second direction, the injection member is retracted into the second housing to prevent an unintentional contact with the injection member. The training container device further includes a plunger component associated with the first housing, said plunger component having an actuation member to simulate delivery of medicament from the first housing, a control interface associated with the device, the control interface including at least one responsive member reactive to a user input, a signal output component associated with the device; and circuitry associated with the device configured to control a provision of the stepwise instructions to the user in the particular sequence.

In another embodiment, a medicament device configured to provide stepwise instructions for using the device to a user in a particular sequence is provided. The device includes a device housing configured to receive a container, the device housing including a control interface, the control interface having at least one responsive member reactive to a user input, a signal output component associated with the device housing, and circuitry associated with the device housing configured to control a provision of the stepwise instructions to the user in the particular sequence. In a further embodiment, the container includes a first housing, and a second housing, wherein the first housing is movable relative to the second housing, and a plunger component associated with the first housing, the plunger component being movable relative to the first housing and the plunger component having an actuation member to execute movement of the plunger in a first direction relative to the first housing.

In a further embodiment, a container for storing a medicament prior to use is provided. The container includes a first housing for containing a medicament, a second housing, wherein the first housing is movable relative to the second housing, and an injection member associated with a lower portion of the first housing. The container further includes when the first housing moves relative to the second housing in a first direction to deliver the medicament, the injection member extends from the second housing traversing a first contaminant barrier disposed at a lower portion of the second housing, and when the first housing moves relative to the second housing in a second direction the injection member is retracted into the second housing to prevent an unintentional contact with the injection member.

In still a further embodiment, a medicament delivery or injection simulation system is provided. The medicament delivery or injection simulation system includes a container, the container having a first housing and a second housing, wherein the first housing is movable relative to the second housing, an injection member or an injection simulation member associated with a lower portion of the first housing, wherein when the first housing moves relative to the second housing in a first direction, the injection member or injection simulation member extends from the second housing traversing a first contaminant barrier disposed at a lower portion of the second housing. The container further including wherein when the first housing moves relative to the second housing in a second direction the injection member or injection simulation member is retracted into the second housing to prevent an unintentional contact with the injection member or injection simulation member, and an actuation mechanism associated with the container, wherein the actuation mechanism drives the movement of the first housing.

BRIEF DESCRIPTION OF THE DRAWINGS

FIG. 3A-3D illustrate the steps of use of an embodiment of the medicament delivery system.

FIG. 4 provides a cross section of a device housing embodiment.

FIG. 5A provides a cross sectional view of a container according to another embodiment.

FIGS. 5B-5G provide an illustration of the steps of use of an embodiment of the medicament delivery system.

FIG. 6 provides a cross sectional view of an injection simulation member embodiment.

FIGS. 7A-7B provide cross sectional views of another embodiment of an injection simulation member.

FIG. 8 provides a cross sectional view of further embodiment of an injection simulation member.

FIGS. 9A-9B provide cross sectional views of another embodiment of an injection simulation member.

FIGS. 10A-10H provide cross sectional views of a barrel cam actuation mechanism embodiment for use with a multiuse medicament device having a device housing.

FIG. 11 provides a schematic illustration of a cam profile for a cam groove of the embodiment of FIGS. 10A-10H.

FIGS. 12A-12E provide cross sectional views of a further embodiment of a barrel cam actuation mechanism for use with a training medicament device.

FIGS. 14A-14D provide cross sectional views of another embodiment of a barrel cam actuation mechanism for use with a single dose medicament device.

FIG. 15 provides a schematic illustration of a cam profile for a cam groove of the embodiment of FIGS. 14A-14D.

FIG. 16A provides a top view of an embodiment of a medicament delivery or injection simulation system with an index cam actuation mechanism illustrating a first step of use of the system.

FIG. 16A' provides a side view of the embodiment of the medicament delivery or injection simulation system shown in FIG. 16A.

FIG. 16B provides a top view of the embodiment of the medicament delivery or injection simulation system shown in FIG. 16A with an index cam actuation mechanism, illustrating a second step of use of the system.

FIG. 16B' provides a side view of the embodiment of the medicament delivery or injection simulation system shown in FIG. 16B.

FIG. 16C provides a top view of the embodiment of the medicament delivery or injection simulation system shown in FIG. 16A with an index cam actuation mechanism illustrating a third step of use of the system.

FIG. 16C' provides a side view of the embodiment of the medicament delivery or injection simulation system shown in FIG. 16C.

FIG. 16D provides a top view of the embodiment of the medicament delivery or injection simulation system shown in FIG. 16A with an index cam actuation mechanism illustrating a fourth step of use of the system.

FIG. 16D' provides a side view of the embodiment of the medicament delivery or injection simulation system shown in FIG. 16D.

DETAILED DESCRIPTION

Figure 1B:
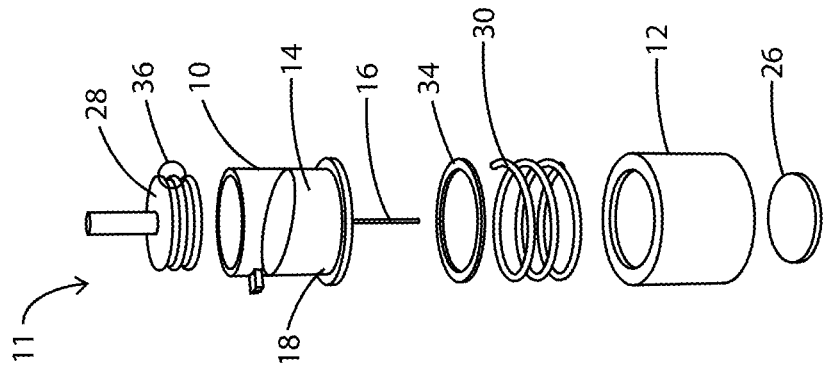
FIG. 1B provides an exploded view of an embodiment of a container.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

Definitions

A "predetermined value" as used herein, for example, includes but is not limited to a value or range of values relating to an event involving use or operation of the device. These may include, but are not limited to thresholds, ceilings, baselines or range values that are desired or undesired for a particular event. Examples of predetermined values include, but are not limited to, a predetermined orientation value, predetermined time value, or a predetermined contact value, in addition to other predetermined values described herein refers to a value that is used as a reference value in relation to a value, signal, or indication that is detected by, for example, a sensor of the delivery training device. Predetermined value may include an optimal value, or a sub-optimal value, or any value there between.

In one example, a predetermined perpendicularity value may include a 90 degree angle between the device and a target region for the device, an additional predetermined perpendicularity value may include a 10 degree angle between the device and a target region for the device. At either predetermined perpendicularity value, or at any value there between, a signal output component may be initiated. The signal output component may therefore be an error message or a congratulatory message, for example.

The term "condition" as used herein includes but is not limited to a user input, a status of the device, anything that is sensed by the device, correct or incorrect stepwise activities, usage of the device over time, among other conditions.

The term "error condition" as used herein includes but is not limited to a condition pertaining to a mistake by the user in using the device, whether the mistake is incorrect positioning or contact between the device and the user, or whether the mistake is an out of order step, a step that exceeds or fails to meet predetermined time value (such as an undue pause during or between steps, or insufficient time for conducting a step or transition between steps). Error conditions may also include errors of the device itself, including low or lack of power or failure to operate as intended.

The term "associated" or "association", as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output. The term "value" as used herein, may refer to a specific value or a range of values.

The inventors have discovered several areas in which the prior art could be improved. Prior art injection devices and syringes have been found by the inventors to lack certain safety and convenient features. While some safety syringes are provided with a retraction-type mechanism, such that after using the syringe, the needle can be retracted into some kind of housing of the syringe, the syringe still requires removing a protective cap from the needle prior to injection. This presents opportunities for unwanted sticking of oneself with the needle. These prior art syringes also present opportunities for contamination of the needle before it is injected into the skin of a user. Another area of the prior art that is lacking in efficiency includes where an auto injector is used for an injection, and the housing is disposed of after a single use. It is not economically efficient to dispose of an auto injector after a single injection. Therefore, the inventors herein have identified a medicament containing container which solves many of these issues found in the prior art.

The subject invention includes, in one embodiment, a container which includes a needle, wherein the container is configured to be received within an injection device, and may be configured to contain a medicament there within. The medicament containing container includes a needle and a safety guard and/or packaging such that the needle is protected and kept sterile until the container is inserted into the injection device in an embodiment. Upon insertion of the container into the injection device, the safety guard is removed and/or the packaging is opened such that the needle is positioned within the injection device for use upon injection by the user. Following injection of the medicament contained within the medicament containing container, the needle automatically retracts into the medicament containing container such that a user cannot access the needle, in an embodiment. Thereafter, the empty container having the needle can be removed or ejected from the injection device and disposed, leaving the injection device ready and able to receive another medicament containing container for the next injection, in one embodiment.

In one embodiment, placing the container into the injection device automatically opens the sterile packaging surrounding the needle portion and/or displaces the safety guard in preparation of the needle for injection. Therefore, the needle and the medicament maintain sterility until the container is inserted into the injection device prior to injection into the patient.

In one particular embodiment, a seal is provided over the needle end of the container to protect the sterility of the container and the needle, prior to its use. During an injection, the needle punctures the seal and traverses the sealed container portion as it exits the proximal end of the injection device into the injection site of the patient.

Following use of the needle for injection, the needle is retracted into the container such that the container can be safely removed from a device housing for disposal. The retraction of the needle into the container prevents unwanted and accidental needle sticks by the patient during the manipulation of the container between its removal from the housing and disposal in a sharps container. Furthermore, in order to comply with regulations regarding needle safety and proper disposal of needles, the retraction of the needle prevents it from being a danger to others, as the needle cannot be accessed once it is retracted within the container.

In one embodiment, the container may be a training (or injection simulation) container, in which an injection simulation member is provided in place of the needle for injection. The training container may be placed within the injection device to assist a user in learning to correctly use the device. The training container may be labeled as a training container, and may contain unique identification information on a portion of the container to identify it as a non-medicament containing container or training container. When the training container is placed within a housing for use, as will be described in greater detail below, the housing may include an information identification reader which identifies the container as a training container. The housing may be a device housing, in one embodiment.

In one embodiment, a medicament delivery system is provided. The medicament delivery system includes device housing, the housing including an actuation mechanism and a receptacle for receiving a container. The actuation mechanism is provided for interacting with the container. The container is provided for storing a medicament prior to use, the container includes a first housing for containing a medicament, a second housing, wherein the first housing is movable relative to the second housing, and an injection member associated with a lower portion of the first housing. The container further includes wherein the actuation mechanism interacts with the container such that the first housing moves relative to the second housing in a first direction the injection member is ejected from the second housing, traversing a first contaminant barrier, the plunger moves relative to the first housing in a first direction to deliver the medicament to the injection member, and the first housing moves relative to the second housing in a second direction such that the injection member is retracted into the second housing to prevent an unintentional contact with the injection member. The container can be removed from the device housing post use and disposed of. In certain embodiments described herein the device housing may be reusable and the container may be removed after use and disposed. In other embodiments, the system may be a single use system, wherein the device housing and in some instances the container is disposed after use. Therefore, in certain single-use embodiments, the container may not be removed from the device housing before disposal of the housing.

In a further embodiment, the actuation member depresses the plunger to deliver the medicament thorough the injection member after the injection member traverses the first contaminant barrier.

In a further embodiment the injection member traverses the first contaminant barrier and the plunger component is depressed so as to deliver the medicament through the injection member. In a particular embodiment, the first contaminant barrier is a membrane.

In still a further embodiment, a first spring is associated with the injection member such that when the first housing moves relative to the second housing in a first direction, the first spring is biased, and when the medicament is delivered from the injection member, the first spring is released and the injection member is retracted into the second housing. In yet a further embodiment, a second contaminant barrier is disposed between the upper portion of the second housing and the lower portion of the first housing to prevent contaminants from entering the second housing. In a further embodiment, a third contaminant barrier is disposed between the plunger and the first housing to prevent contaminants from entering the first housing and/or the medicament. Examples of contaminant barriers include but are not limited to membranous materials or membranes or other materials or components know to those of skill in the art to prevent unwanted contaminants from entering the device. O-ring type membranes or contaminant barriers may be used in the second and third contaminant barrier positions, in non-limiting examples. A membrane may be used as a contaminant barrier in the first contaminant barrier position, in another non-limiting example.

The container may be manually actuated by pressing down on the stopper, in one embodiment. Alternatively, in a non-limiting example, the container may be actuated with an actuation mechanism, wherein the actuation mechanism may be rotatable as an index cam, in one non-limiting example, which may be activated manually via a torsion spring or by motor, gas, or compressed air, among other activation means known to those of skill in the art. Alternatively, the container may, itself, be actuated via a motor, gas or compressed air. Any other means of activation or actuation of the container to deliver medicament known to those of skill in the art are contemplated herein.

In a further embodiment, the medicament delivery system is provided wherein the first housing includes at least a first projection member that interacts with the actuation mechanism to cause the first housing to move relative to the second housing such that the injection member traverses the first contaminant barrier when the actuation mechanism is activated.

In another embodiment, the medicament delivery system is provided wherein when the actuation mechanism is activated, the actuation mechanism interacts with a portion of the first housing to move the first housing in a first direction relative to the second housing such that the first spring is biased and the injection member traverses the first contaminant barrier.

The actuation mechanism can be activated in various ways, for example, by depressing an actuation member, by turning a switch or by contact with a portion of the medicament delivery system, or by inserting the container into the housing, for example.

In another embodiment of the medicament delivery system, a first spring is disposed between the lower portion of the first housing and a lower portion of the second housing, and a second spring is disposed between the plunger and the actuation member. In a further embodiment, the second spring includes a greater resistance than the first spring, such that by activating the actuation member, the first spring is compressed before the second spring and the injection member traverses the contaminant barrier in the second housing before the medicament is delivered from the injection member. The system may vary to compensate for different forces required to inject or simulate an injection for delivery of a medicament using the system. In one example, one force may be needed to force a needle to puncture the skin of a user with the system, wherein another force may be needed to disperse/deliver a medicament from a medicament delivery system to a user. The subject invention can vary to compensate for these different forces. In one non-limiting embodiment, springs of varying resistances may be used.

In an embodiment of the medicament delivery system, the actuation mechanism may be a rotatable member. The rotatable member may include a first threaded portion and a second threaded portion, in one embodiment. The second threaded portion may be provided to interact with an optional projection member of the container such that when the actuation mechanism is rotated in a first direction, the second threaded portion moves the projection member in a first direction relative to the second housing, such that the spring is biased and the injection member may be extended through the first contaminant barrier. In a further embodiment, the first threaded portion of the actuation mechanism may be provided to interact with the upper portion of the plunger component such that when the actuation mechanism is rotated in a first direction, the first threaded portion moves the plunger component relative to the first housing in a first direction to deliver the medicament through the injection member. One skilled in the art in view of the teachings herein would understand that the first threaded portion could associate with a top portion or other portion of the first housing to move the first housing in a first direction relative to the second housing.

In another embodiment, the second threaded portion contacts the projection member to move the first housing in a first direction relative to the second housing before the first threaded portion of the rotatable member contacts the upper portion of the plunger component to move the plunger component in a first direction relative to the first housing to dispel or deliver the medicament through the injection member.

In a further embodiment, the second threaded portion of the rotatable member includes an opening through which the projection member may be released, such that the first housing moves in a second direction relative to the second housing, to retract the injection member into the second housing and prevent unintentional contact with the injection member. The rotatable member may be rotated by a motor or a torsion spring, or by hand in some embodiments, or a combination thereof, or any other means of rotation of the rotatable member known to those of skill in the art.

In an embodiment, the container includes a unique identification information of the medicament contained within, whereby the identification information can be read by an identification reader. The device housing may include an identification reader and/or the actuation mechanism may include an identification reader, in certain embodiments. The container information component and container information component reader may interact with one another such that information identified by the reader can be provided to the user. The information may be provided to a user on a display, or another visual communication device, or audibly provided to the user. The information may further be provided with a smell or a vibration, or by any other method of communication known in the art. The information may be provided, for example, by way of a bar code, or by a specific shape on the container which can be read by the reader to identify specific information about the medicament contained within the container. Such information may include the name and strength of the drug, the expiration date, dose, manufacturer's name, batch number, proper handling instructions (e.g., temperature storage conditions) among other information.

The container information component may further be designed to identify and record particular information regarding the container and the medicament stored within, such as, for example the temperature at which the container has been maintained from the manufacturer through the delivery process. A log may be recorded by the system of the varying temperatures of the container and the medication by a module of the container so that a user can identify if the container has been maintained at a proper temperature prior to use of the medicament. For this and other purposes, the container may include a power source such as a battery, for example. Therefore, medicaments which have not been maintained at the proper storage/handling temperature can be discarded. In instances where the container information component reader identifies information on the container information component, such as, for example, information that the container is housing an expired medication, the safety mechanism will prevent an activation of the actuation device, and therefore prevent injection of the expired medication into the user, in a non-limiting example.

In another embodiment, the medicament delivery system is provided wherein the actuation member or actuation mechanism interacts with the plunger such that the first housing to moves in a first direction relative to the second housing such that the injection member traverses the first contaminant barrier when the actuation member is activated. In a further embodiment, thereafter, the actuation member interacts with the plunger such that the plunger moves in a first direction relative to the first housing so as to deliver the medicament to the injection member, and the first housing moves relative to the second housing in a second direction such that the injection member is retracted into the second housing to prevent an unintentional contact with the injection member. When the actuation member or actuation mechanism is activated, the first housing moves in a first direction relative to the second housing to eject the injection member through the first contaminant barrier before the plunger moves in a first direction relative to the first housing to deliver the medicament to the injection member and to a subject, in one embodiment.

In a further embodiment, as described above, the actuation mechanism may be a rotatable member, in one non-limiting example the rotatable member is an index cam. The rotatable member includes a first threaded portion, the first threaded portion provided to interact with an upper portion of the plunger component such that when the actuation mechanism is rotated in a first direction, the first threaded portion moves the first housing in a first direction relative to the second housing such that the spring is biased and the injection member may be extended through the first contaminant barrier. In a further embodiment, thereafter, the actuation mechanism interacts with the plunger component such that the plunger component moves in a first direction relative to the first housing so as to expel the medicament through the injection member, and the first housing moves relative to the second housing in a second direction such that the injection member may be retracted into the second housing to prevent an unintentional contact with the injection member. When the actuation mechanism is activated, the first housing moves in a first direction relative to the second housing to extend the injection member through the first contaminant barrier before the plunger component moves in a first direction relative to the first housing to expel the medicament through the injection member and to a subject, in one embodiment. This can occur with only a first threaded portion which interacts with the plunger component, in one embodiment. In a further embodiment, the first threaded portion includes an opening through which the projection member may be released, whereby the spring may be released, such that the first housing moves in a second direction relative to the second housing, and the injection member retracts into the second housing.

The system operates in such a manner due in part at least to a difference in resistance between the movement of the first housing relative to the second housing and the ejection of the injection member through the first contaminant barrier and the resistance between the movement of the plunger relative to the first housing to dispel the medicament through the injection member. The first action will occur before the second as the system will take the path of least resistance. Thus, there is less resistance associated with the movement of the former than there is associated with the latter.

The actuation mechanism(s) can be activated by a torsion spring or a motor, or a combination thereof. Those skilled in the art will appreciate that other forces and devices may be used to activate the actuation mechanism(s) in such a manner to activate the components of the device as described herein. Those skilled in the art will appreciate that other forces and devices may be used to rotate the rotatable member in such a manner to depress the components of the device as described herein.

In a further embodiment, a medicament delivery and simulation system is provided, the system including a container, the container including a first housing, a second housing, wherein the first housing may be movable relative to the second housing and an injection member or an injection simulation member may be associated with a lower portion of the first housing. When the first housing moves relative to the second housing in a first direction, the injection member or injection simulation member extends from the second housing traversing a first contaminant barrier disposed at a lower portion of the second housing, and when the first housing moves relative to the second housing in a second direction the injection member or injection simulation member may be retracted into the second housing to prevent an unintentional contact with the injection member or injection simulation member. The medicament delivery and simulation system further includes an actuation mechanism in association with the container, wherein the actuation mechanism drives the movement of the first housing and/or the second housing. In a further embodiment, the actuation mechanism includes a motor. The actuation mechanism may include a motor, an index cam, a plunger component, or any manually or electrically activated actuation mechanism, in non-limiting examples. Other actuation mechanisms known to those of skill in the art are contemplated herein.

In a further embodiment, the medicament delivery and simulation system is provided wherein the first contaminant barrier is a membrane. In one embodiment, the container includes a medicament. In still a further embodiment, a stopper may be associated with the first housing, the stopper being movable relative to the first housing, whereby the medicament may be delivered through the injection member upon movement of the first housing relative to the second housing in a first direction followed by movement of the stopper relative to the first housing in a first direction. The simulation member may include an injection simulation member such as a needle simulator as described herein, for example.

In yet a further embodiment, the actuation mechanism may be a motor which drives the movement of the stopper. In yet another embodiment of the medicament delivery and simulation system, the system further includes a second contaminant barrier between an upper portion of the second housing and the lower portion of the first housing to prevent contaminants from entering the second housing. In still a further embodiment, a third contaminant barrier may be disposed between the stopper and the first housing to prevent contaminants from entering the first housing and/or the medicament, alternatively the stopper includes a third contaminant barrier or the stopper may be associated with the third contaminant barrier. In another embodiment, a shaft may be connected to the stopper.

In a further embodiment, the system includes a device housing having a receptacle for receiving the container. In still a further embodiment, the actuation mechanism is in the device housing.

In another embodiment, a medicament device configured to provide stepwise instructions for using the device to a user in a particular sequence is provided. The device includes a device housing configured to receive a container, the device housing having a control interface, the control interface having at least one responsive member reactive to a user input, an actuation member and/or actuation mechanism configured to interact with the container, a signal output component associated with the device housing, and circuitry associated with the device housing configured to control a provision of the stepwise instructions to the user in the particular sequence.

In a further embodiment, the container includes a first housing and a second housing, a spring disposed between a lower portion of the first housing and a lower portion of the second housing, wherein the first housing is movable relative to the second housing, and a plunger component associated with the first housing. The plunger component is movable relative to the first housing, wherein the actuation member or mechanism interacts with the container to move the first housing in a first direction relative to the second housing, and the plunger in a first direction relative to the first housing. In a further embodiment, the medicament device includes a training mode and/or a medicament delivery mode. A switch or a button can be used to change from training mode to medicament delivery mode or vice versa, in some embodiments. Alternatively, in an embodiment, insertion of a training container into the device housing can automatically select the training mode of the device. Also, insertion of a container containing a medicament can automatically turn on the medicament delivery mode of the device, in some embodiments.

In one non-limiting example, the stepwise instructions are audibly provided to the user via the signal output component. The instructions can be a recording of any language providing verbal instructions. Alternatively, the instructions may be given with a series of sounds or beeps or other audible notifications to a user. In other embodiments, the instructions may be provided by one or a series of vibrations of the system or a scent or taste or temperature change of the system or the housing. Instructions may alternatively be provided visually, wherein a textual instruction may be provided or a pictorial or video-type instruction. Various lights may also be used to signal the stepwise instructions to a user via a series of lighted portions on the housing signaling the steps in which the system may be used, or any other lighted signaling manner as known by those of ordinary skill in the art. Any of these sounds, visual guides, vibrations, tastes or smells may be provided via the signal output component, in one embodiment.

In one embodiment, the medicament device is provided wherein the container includes an injection member associated with a lower portion of the first housing, and wherein the first housing includes a medicament, such that activation of the actuation member forces the plunger to move in a first direction relative to the first housing to deliver the medicament to the injection member after the first housing moves in a first direction relative to the second housing to eject the injection member through a first contaminant barrier disposed at a lower portion of the second housing, and the first spring is biased. In a further embodiment, the first housing moves relative to the second housing in a second direction, such that the first spring is released and the injection member is retracted into the second housing to prevent an unintentional contact with the injection member.

After an injection has occurred and the injection member is retracted into the second housing, the used container can be removed from the device housing and disposed. A new container containing either the same or a different medicament or a training container can be inserted in its place into the device housing.

In another embodiment, the container includes an injection simulation member associated with a lower portion of the first housing, wherein the plunger moves relative to the first housing in a first direction to simulate delivery of medicament from the first housing after the first housing moves relative to the second housing in a first direction to eject the injection simulation member from the second housing, and bias a first spring disposed between a lower portion of the first housing and a lower portion of the second housing. The injection simulation member is provided to allow for a simulated injection experience during use without puncturing the skin of a user. In one embodiment, activation of the actuation member forces the plunger to move in a first direction relative to the first housing.

The injection simulation member may include a blunt end probe or other similar object known in the art provided to mimic the sound, look, and/or feel of the injection by an injection member (in one example, a needle) in a training/simulation session without puncturing the skin of the user. One skilled in the art would realize that the injection simulation member can be made of any materials known in the art to provide the flexibility, and tensile modulus while maintaining the rigidity and stability to provide a simulated sensation of an injection without traversing the skin of a user. The injection simulation member provides a perception to a user of injection into the skin and mimics or simulates an actual injection, wherein the injection simulation member is activated and retracted like the injection member described herein, however, an injection (i.e., puncture of the skin) does not occur.

In a further embodiment, activation of the actuation member forces the plunger to move in the first direction relative to the first housing. In still a further embodiment, a first contaminant barrier is disposed at a lower portion of the second housing, and wherein the injection simulation member traverses the first contaminant barrier when the injection simulation member is ejected from the second housing. In a further embodiment, the first spring is released such that the first housing moves relative to the second housing in a second direction to retract the injection simulation member into the second housing to prevent an unintentional contact with the injection simulation member. In another embodiment, the injection simulation member is configured to extend through a membrane in the lower portion of the second housing when the actuation member is activated, forcing the injection simulation member through the opening, such that the injection simulation member simulates the force and motion of an injection member without being inserted into the user or delivering medicament to the user.

In trying to simulate an actual medicament delivery or injection device, the device herein requires a certain force by the user for activation of the device. Multiple forces can be simulated by the device such as the force that must be used (e.g. manual, spring loaded, electric motor, pneumatic cartridge, ultrasonic) to force a needle to puncture the skin in an injector or an auto-injector device. In another example, a different force may be needed to disperse a medicament from a medicament delivery device into a user. The medicament device can vary to compensate for these different forces so as to replicate the force of the actual medicament delivery device being simulated. Additional forces such as that used to push a fluid through the needle of a medicament delivery device (manual, spring loaded, electric motor, pneumatic cartridge, ultrasonic) can also be simulated by the medicament device so as to reduce anxiety of the user in using the medicament delivery device.

The medicament device including the medicament delivery simulation mechanism provides tactile, visual, and auditory stimuli to a user, wherein during the training, the tactile, visual, gustatory, olfactory, or auditory feedback, or any combination thereof, are synchronized in a manner such that an actual delivery device is simulated. The synchronization of the stimuli is significant in facilitating multisensory learning of the user.

Following actuation of the device, a re-setting of the device may be necessary. This can be accomplished manually and mechanically, in one example, by pressing the portion of the device with the ejected medicament simulation member against a surface until the ejected member is re-inserted into the housing of the device. Other re-setting mechanisms will also be discussed herein.

Powering on the device, in some embodiments, initiates or activates the stepwise instructions to the user. However, the instructions may be initiated or activated by any suitable means known in the art. For example, in another embodiment, activation of the actuation member may initiate the stepwise instructions of the device. In yet another embodiment, the stepwise instructions may be initiated by moving the device, which may be recognized via a motion sensor on or associated with the device. In still another embodiment, a user input via the responsive member of the device may activate or initiate the instructions. The device may include a safety mechanism to prevent unintended actuation of the actuation member. The safety mechanism may include a manual lock and unlock safety lock, a button on the device which locks and/or unlocks the device, locking member within the container of the device which prevents unintentional actuation of the device unless the container is placed within a housing or manually unlocked, or any other safety mechanisms to prevent unintended actuation of the actuation member as known in the art.

The medicament device may further include at least one responsive member that is reactive to user input. The responsive member may include a button, either virtual or non-virtual, a switch, a touch sensor, a toggle, a heat or tactilely sensitive response sensor, or any combination thereof, or any other such device as known in the art. The responsive member may be part of the control interface of the device. Alternatively, or in addition to being disposed on the device, at least one responsive member can be in association with the device. The control interface can be used for generating user commands, and the circuitry disposed within the device or in association with the device is in communication with the control interface. The circuitry may be embodied as a processor-based circuit, wherein it is configured and arranged to receive input from the user via the control interface, wherein the processor-based circuit includes an audio signal processor configured and arranged to provide audio to the user to instruct the user while using the medicament device during the medicament delivery or simulation/training, wherein the audio is controlled by the responsive member on the control interface via user input.

In another embodiment, the medicament delivery device and/or the device housing includes a sensor to detect a condition of the device. The sensor may be disposed on the device or associated with the device. In still a further embodiment, an output of the device from the signal output component is initiated in response to a predetermined value detected for a condition. In one embodiment the sensor is an orientation sensor, provided to detect an orientation of the device. In a further embodiment, the signal output component is initiated if the detected orientation of the device meets a predetermined orientation. Certain medications may require certain modes of delivery or application, and may dictate the orientation of the device during delivery. The orientation sensor is useful in identifying the proper orientation for the device based on the medicament being administrated or the type of delivery device.

In a further embodiment, the sensor is a contact sensor provided to detect a contact between the device and the user. In still a further embodiment, the signal output component is initiated if the detected contact of the device meets a predetermined contact value. The contact sensor may be provided to detect a contact or an insufficient contact between the device and the user, wherein the signal output component is initiated if the contact of the device meets a predetermined contact value, or in other instances if the contact of the device fails to meet the predetermined contact value. This predetermined contact value may be set at 100% contact between the device and the portion of the body of the user being used for the delivery of the medicament, or the contact value may be set between 90-99%, or 80-88% contact such that a user can be made aware when there is sufficient contact between the device and the user for adequate delivery of the medicament from the device. Additionally, or alternatively, in some circumstances contact sensors may be provided on the portion of the device which is intended to contact the surface of the user where delivery of the medicament is to occur, therefore the contact sensor can alert the user when sufficient contact has been made. The contact sensor can also alert the user when sufficient contact has not been made with the surface of the user.

In yet another embodiment, the sensor is a perpendicularity sensor provided to detect the perpendicularity of the device relative to a surface of the user. In another embodiment, the signal output component is initiated if the detected perpendicularity of the device meets a predetermined perpendicularity value. The perpendicularity sensor can sense the angle created between a longitudinal axis of the device and the surface of the user where the delivery of the medicament is to occur. The predetermined perpendicularity value takes into account the best angle or range of angles provided between the device and the user within which to deliver the medicament. This value may vary based on the type of medicament being delivered. In some instances, a right angle between the device and the surface of the skin of the user may be the optimal perpendicularity value. However, in other instances, the predetermined perpendicularity value may range from a 10 degree angle to a 45 degree angle or a 50 degree angle to a 90 degree angle. Perpendicularity sensors which incorporate the use of a light on the device may be used to properly align the device relative to the user prior to use.

In another embodiment, the sensor is provided to detect alignment of the device during the medicament delivery and/or simulation. As described above in one example perpendicularity is alignment. In still another embodiment, the signal output component is initiated if the detected alignment of the device meets a predetermined alignment value.

In still another embodiment, the sensor is provided to detect a location of the device for the medicament delivery simulation. In a further embodiment, the signal output component is initiated if the detected location of the device meets a predetermined location value. In still another embodiment, the sensor is provided to detect a location of the device for the medicament delivery simulation; the signal output component may be initiated if the detected location of the device meets a predetermined location value. The location for the medicament delivery is important with a medicament in which the location for delivery on the body of the user must rotate from one place to another. Oftentimes the recommended application of medicaments to the body requires rotation of the location of administration. For example, the first administration of the medicament may be on the arm, whereas the next application of the medicament may be on the thigh region, such that the locations of application on the body of the user are rotated. The movement of the location of the administration may prevent to some extent any one location from becoming overused, sensitive, bruised, or damaged over the course of the treatment.

Additional sensors of the medicament device include proximity sensors, resistive sensors, and tactile sensors, temperature sensors, alignment sensors, accelerometers, gyroscopes, and perpendicularity light sensors or any other sensor suitable for detecting one or more of the conditions associated with the device and for assisting the user in the proper use of the device during training and/or delivery of medicament.

In yet another embodiment, an output of the device from the signal output component is initiated in response to a predetermined elapsed time value occurring within the particular sequence of stepwise instructions. In one embodiment, the predetermined elapsed time value period includes a pause between the steps of the stepwise instructions. In another embodiment, the output of the device from the signal output component is initiated when the user performs one or more steps in the particular sequence within a predetermined time period.

In a further embodiment, the condition detected is an error condition. In a further embodiment, the error condition is a use of the device in an incorrect sequence. In yet a further embodiment, the error condition is a failure to complete a step in the use of the device. In still a further embodiment, the error condition is a failure by the user to use the device to perform one or more steps in the particular sequence within a predetermined time period.

In another embodiment, the medicament device may include a memory module. The memory module may include information regarding a condition of the user of the device, in one embodiment. In a further embodiment, the memory module may be removable. In a further embodiment, the memory module includes different languages of a script for guiding the user through the steps of the training.

In another embodiment, the medicament device is provided wherein the signal output includes an audio output, wherein the audio output can be provided in one or more languages. In still a further embodiment, the device includes an indicator that conveys information about a condition of the device. In one embodiment, the indicator may indicate that a training or delivery of a medicament is complete, for example. Oftentimes with injection devices, the injection member must be maintained in the skin of the user for a period of time after the injection is complete. The indicator herein may indicate to a user once the period of time has elapsed for which the injection member must be kept into the skin at which time the injection member is retracted into the device. In some instances this time period is referred to as a "dwell period". Otherwise the injection member may only indicate to a user once the entire process has been completed and the injection member is retracted. Additionally, the indicator could provide a count-down of the amount of time remaining left in the injection (medicament delivery) or in the training.

In another embodiment, the control interface includes a display to provide information to the user. The control interface of the device may provide the user with the ability to change the language of the audio output of the device. Languages that the audio output may be communicated to a user include but are not limited to, English, Spanish, French, Arabic, Portuguese, Russian, Chinese, and Japanese. It is known by those of skill in the art that any language may be provided via the audio output of the device.

In still another embodiment, the signal output component generates a visual output including at least one light or screen display, or a combination thereof. In yet another embodiment, the signal output component of the device generates an audio output wherein the audio output includes a sound or a series of sounds.

In another embodiment, the medicament device may be connected to or associated with an external source, such that information can be communicated to and/or from the device. The information transferred to and/or from the device includes at least one computer readable file, in one embodiment. The information may include usage of the device by the user such as date and time and frequency information. The information may include effectiveness of the usage of the device by the user, or information about errors of the user or of the device. Some of this information may be provided to a physician of the user or a parent or legal guardian or spouse or other family member of the user of the device. The information may be communicated to a manufacturer to provide relevant information about the device and problems associated therewith.

In another embodiment, the information communicated to and/or from the device includes at least one computer readable file. Such files may include videos not limited to but including training videos. Other information which may be communicated to and/or from the device includes information regarding performance of the user in using the device, trending data regarding the use of the device and the operation of the device itself, software information, updated software, language software information, and any other information that would be beneficial to the use and/or operation of the device. The communication of information or data to and/or from the device may occur via a wire or wireless connection, and the information may be communicated to and/or from a network, a computer, a system, or to and/or from another device. In a further embodiment, the medicament device includes a program code module, wherein the program code module records a condition of the device.

In one embodiment, the condition detected by the device is a user input. In another embodiment, the condition is a status of the device. In a further embodiment, the condition includes an input sensed by the device. In still another embodiment, the condition includes correct or incorrect stepwise activities by the user of the device. In a further embodiment, the condition includes usage of the device, a status of the device, anything sensed by the device, usage of the device over time, user input. The condition detected may be an error condition. In a further embodiment, the error condition is a use of the device in an incorrect sequence. In yet a further embodiment, the error condition is a failure to complete a step in the use of the device. In still a further embodiment, the error condition is a failure by the user to use the device to perform one or more steps in the particular sequence within a predetermined time period.

In a further embodiment of the device, when the user reaches a step in which an error was made by the user in a previous training, an output of the device is initiated to alert the user to the previous error in the step. This serves to help the user through the step in which the previous error was made by emphasizing the instructions at that step to prevent future error at that step. The emphasis may be in the form of augmented output by increasing the volume of the audible output, repeated instructions or providing instructions at that step at a slower pace where the audible output includes instructions, changing the characteristics of the output whether it be a flashing light wherein the rate of flashing changes, or a color change in a light, or providing a different audible sound such as a beep, a musical tone, or a different alarming sound, furthermore the output may include a vibration of the device or other such warning to the user as is known in the art.

In one embodiment, the medicament device includes a safety mechanism to prevent unintended actuation of the actuation member. The safety mechanism may include a manual lock and unlock safety lock, a button on the device which locks and/or unlocks the device, locking member within the container of the device which prevents unintentional actuation of the device unless the container is placed within a housing or manually unlocked, or any other safety mechanisms to prevent unintended actuation of the actuation member as known in the art.

In an embodiment, the program code module can be incorporated as part of the device, connected to the device, in communication with the device, or in sync with the device. For example, when a user is not using the medicament delivery training device on a regular basis (regular basis can be identified by a predetermined, pre set time period), the device will record the usage of the device, and may be configured to alert a user or an outside personnel such as a physician, for example, of the recorded usage. The alert may indicate the amount of training or simulation that has been recorded by the device, or the accuracy or inaccuracy with which the device is being used. Examples of user compliance which may be recorded by the device include correct and incorrect use of the device. The program code module can be used to indicate to the user or outside personnel, a physician for example, whether the user is correctly and accurately using the device.

Alternatively, or in addition, the program code module may provide the user information relating to his or her use of the device including the amount of training or simulation accomplished as well as feedback regarding the quality of training or actual medicament delivery recorded. The program code module may also provide the user of the device with areas of improvement in the medicament delivery or simulation steps, or may provide the user with positive feedback regarding areas where the user has complied with the steps or use of the device. The program code module can include a records and statistical analysis feature, and can download and/or transfer records to and from the device. This program code module may be helpful in research and development of the device. With the use of the program code module recording and tracking various features and uses of the device, one can readily determine areas in which the device may be improved. The program code module also includes graphing capability of recorded data, as well as data trending results of the performance of the device and/or the user, the efficiency of the user and of the device in training and/or simulation. As part of the program code module, features such as an alarm or indication (visual, auditory, tactile . . . etc.) to the user of the device or to another can be initiated if the data received and analyzed by the module is out of range or is trending out of range (a range will be pre-determined).

As will be appreciated by one of skill in the art, certain examples of the present invention may be embodied as a device or system having a processing module, and/or computer program product having at least one program code module. Accordingly, the present invention may take the form of an entirely hardware embodiment or an embodiment combining software and hardware aspects, commonly known as firmware. As used herein, firmware includes a computer program module that is embedded in a hardware device, for example a microcontroller. It can also be provided on flash memory or as a binary image file that can be uploaded onto existing hardware by a user. As its name suggests, firmware is somewhere between hardware and software. Like software, it is a computer program which is executed by a microprocessor or a microcontroller, but it is also tightly linked to a piece of hardware, and has little meaning outside of it.

The term "microprocessor" may include a single processing device or a plurality of processing devices. Such a processing device may be a microcontroller, digital signal processor, microcomputer, central processing unit (CPU), field programmable gate array (FPGA), programmable logic device, state machine, logic circuitry, analog circuitry, digital circuitry, and/or any device that manipulates signals (analog and/or digital) based on operational instructions. The microprocessor may have operationally coupled thereto, or integrated therewith, a memory device or a memory module. The memory device or memory module may be a single memory device or a plurality of memory devices. Such a memory device may be a read-only memory, random access memory, volatile memory, non-volatile memory, static memory, dynamic memory, flash memory, and/or any device that stores digital information. A computer, as used herein, is a device that includes at least one processing module, and optionally at least one memory device.

The circuitry of the device may include at least in part, the microprocessor, the signal output component for initiating audio, and visual, outputs, among other electronic components. The components may be operatively coupled by electrical conductors, however, in other embodiments the components may be operatively coupled without being physically connected. For example, in some embodiments, at least a portion of the components included in an electronic circuit system can be inductively coupled. In other embodiments, at least a portion of the components included in an electronic circuit system can be evanescently coupled.

The circuitry of the device may include a flexible printed circuit board to electronically couple with the components contained therein. The circuitry may be disposed in any suitable manner relative to the housing of the device, or may be associated with the housing of the device. In some embodiments, for example, the circuitry can be integrated with the simulated medicament delivery training device. The circuitry can be contained within the housing, and/or it may be partially or fully assembled concurrently with and/or with the same processes of the medicament delivery training device, the circuitry may alternatively or in addition be provided on the outer portion of the housing of the device.

In yet another embodiment, a non-transitory computer-readable medium embedded in a medicament delivery training device is disclosed. The non-transitory computer readable medium stores instructions executable by the microprocessor or another processing device to cause the processing device to output audio via the signal output component in the medicament delivery training device in response to an activation of a responsive member on a control interface of medicament delivery training device to guide a user through the stepwise instructions for operation of the medicament delivery training device in response to the user input and to instruct the user to actuate the actuation member of the device to simulate an actual medicament delivery in response to an actuation of the actuation member of the device.

Some embodiments of the invention relate to a computer storage product with a computer-readable medium having instructions or computer code thereon for performing various computer-implemented operations. The media and computer code may be those specially designed and constructed for the purposes of the invention, or they may be of the kind well known and available to those having skill in the computer software arts. Examples of computer-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks; carrier wave signals; and hardware devices that are specially configured to store and execute program code, such as Application-Specific Integrated Circuits ("ASICs"), Programmable Logic Devices ("PLDs"), and ROM and RAM devices. Examples of computer code include, but are not limited to, micro-code or micro-instructions, machine instructions, such as produced by a compiler, and files containing higher-level instructions that are executed by a computer using an interpreter. For example, an embodiment of the invention may be implemented using Java, C++, or other object-oriented programming language and development tools. Additional examples of computer code include, but are not limited to, control signals, encrypted code, and compressed code.

The data storage modules may include a storage medium component(s) such as, but not limited to, an electronic, magnetic, optical, electromagnetic, infrared, or semiconductor system, apparatus, device, or propagation medium. More specific examples (a non-exhaustive list) of the computer-readable medium would include the following: a portable computer diskette, a random access memory (RAM), a read-only memory (ROM), an erasable programmable read-only memory (EPROM or Flash memory), an optical fiber, a portable compact disc read-only memory (CD-ROM), a DVD (digital video disk), or other electronic storage medium.

Computer program code modules for carrying out operations of certain embodiments of the present invention may be written in an object oriented, procedural, and/or interpreted programming language including, but not limited to, Java, Smalltalk, Perl, Python, Ruby, Lisp, PHP, "C", FORTRAN, Assembly, or C++. The program code modules may execute entirely on the device, partly on the device, as a stand-alone software package, partly on the device and partly on a remote computer or device or entirely on the remote computer or device. In the latter scenario, the remote computer or device may be connected to the user's device through a local area network (LAN) or a wide area network (WAN), or the connection may be made to an external computer (for example, through the Internet using an Internet Service Provider).

The medicament device may further include a training mode and/or a delivery mode, in one embodiment, so that a user can switch between the modes of use on the device. The device can be used both for training and for delivery of a medicament to the user. In the training mode, a training container device with a simulated injection member is used. In the delivery mode a container device with an injection member (such as a needle, for example) is used. The device may be arranged such that a user must select the particular mode desired for use. In another embodiment, the device may recognize the container device placed within the device housing and automatically detect whether a training mode or a delivery mode is desired based on the container received within the device housing. The devices and systems are described herein as multi-use devices and systems; however, they can also be used as single-use system and devices which are disposable.

In a further embodiment, the container includes a container information component, wherein the container information component includes information of the medicament contained in the container. Such information may include, for example, the name of the medicament, expiration date, manufacturer name and information, medicament strength, dosage, batch number, lot number, storage conditions, directions for use, brand/generic information, among other pertinent information regarding the medicament. In a further embodiment, the reusable component includes a container information component reader, wherein said container information component reader can read information contained in or on the container information component. In a further embodiment, the output component provides an output to the user based on the information read by the container information component reader.

In another embodiment, at least one switch is disposed within the device housing, such that when the container is received within the device housing, the at least one switch is activated. In a further embodiment, activation of the at least one switch powers on the medicament device. In yet a further embodiment, inactivation of the at least one switch by removing the container from the device housing powers off the medicament device. In still another embodiment, activation of the at least one switch initiates the stepwise instructions of the medicament device to the user, and/or stops the stepwise instructions from being provided to the user from the medicament device.

In some embodiments, the devices provided herein are associated with a memory storage module which may be either a removable or a non-removable memory storage module. Memory contained in this module may include various languages of audio, updating information for the device, information about various medical conditions and medicaments including usage, storage, and any other important information associated therewith. The memory module may further include a script for guiding the user through the steps of the medicament delivery simulation/training. The script may be provided in any language as described above.

In some embodiments, the devices may further include a skin type measuring device or module used to detect the type of skin of the user as is provided in US Patent Application Publication US 2008/0265170A1 by Ales et al, or any other type of skin type measuring device or module as known in the art. The device may also detect differences between skin at various locations on a body, differences between the skin of different age groups, ethnicities, genders, etc., to assist a user in determining a location for medicament delivery. In some embodiments, the device may record and informs a user of the last medicament application site and direct a user to the next medicament application site on the body; this information may be provided in a rotation. The device can additionally instruct a user on the optimal method for applying or injecting the particular medicament (subcutaneous, intramuscular, etc.), or the ideal location on the user for applying or injecting the medicament (buttocks, arm, thigh, etc.).

The system and device may further include, in some embodiments, a reminder feature to remind the user to use the device by initiating a signal output. The reminder can be initiated by the signal output of the device, and as described above can be auditory, visual, tactile or any other type of output described in other embodiments herein, and any additional output known to those of skill in the art. The reminder feature of the device may also remind a user of an upcoming appointment with a physician appointment, or appointment with another health care professional.

In another embodiment, the medicament delivery system may include a locking mechanism disposed adjacent to the first and/or second housing so as to prevent movement of the plunger in a first direction relative to the first housing and the first housing in a first direction relative to the second housing when the locking mechanism is activated. In a further embodiment, insertion of the container into the receptacle of the device housing inactivates the locking mechanism. In another embodiment, removal of the container from the receptacle of the device housing activates the locking mechanism disposed adjacent to the second housing so as to prevent movement of the first housing in a first direction relative to the second housing and/or the second housing in a second direction relative to the first housing. The locking mechanism can be arranged in the system and device such that pre-delivery of the medicament or pre-simulation, the first and second housings cannot move relative to one another, and plunger cannot move relative to first housing and post-delivery or post-simulation the first and second housings cannot move relative to one another, but the plunger is freely movable.

Illustrative Embodiments

Figure 1A:
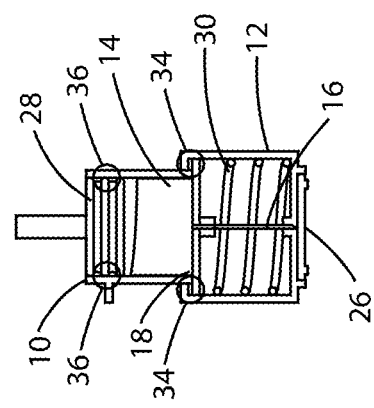
FIG. 1A provides a cross-sectional view of an embodiment of a container.

Turning to the Figures, FIG. 1A provides a cross-sectional view of an embodiment of a container 11, the container 11 including a first housing 10, a second housing 12, an injection member 16 and a first spring 30 disposed between a lower portion of the first housing 18 and a lower portion of the second housing 22. The container 11 further includes a first contaminant barrier 26 disposed at a lower portion of the second housing 22. A plunger component 28 is provided associated with the first housing 10. The plunger component 28 may include a stopper 28B and a shaft 28A in an embodiment, as shown in FIGS. 1A-1B. A third contaminant barrier 36 is disposed between the plunger component 28 and the first housing 10 and prevents contaminants from entering the first housing 10 contacting a medicament 14 contained within the first housing 10. A second contaminant barrier 34 is disposed between the second housing 12 and the first housing 10 to prevent contaminants from entering the second housing and contacting an inner portion of the second housing 12 and the injection member 16. The injection member 16 may be, for example, a needle in one embodiment. FIG. 1B provides an exploded view of the embodiment of the container 11 provided in FIG. 1A. In FIG. 1B, the second contaminant barrier 34 is embodied as an o-ring type seal, however, different types of contaminant barriers or seals can be used. This embodiment is provided for example, only and not in a limiting capacity. A projection member 40 is provided in FIGS. 1A-1B, the projection member 40 can be used to interact with the actuation mechanism 91 as is described in more detail below. It will be apparent to those skilled in the art, in view of the teachings herein that, the projection member 40 is an optional feature, and is not required for operation of the container 11, depending on the type of actuation implemented.

Figure 2B:
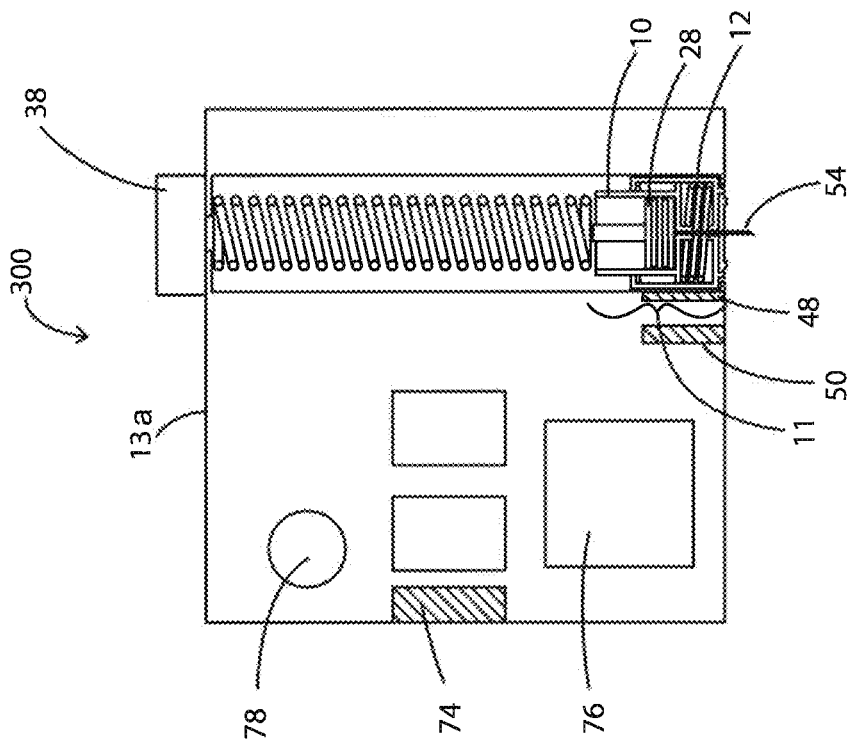
FIG. 2B provides a cross-sectional view of an embodiment of a medicament device.
Figure 2A:
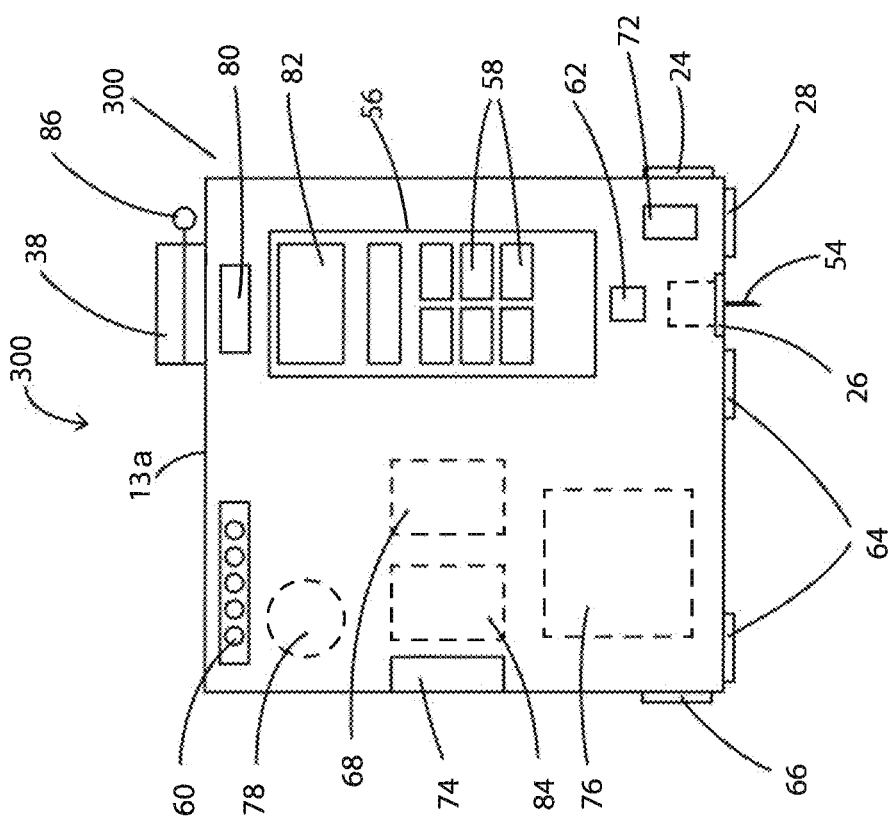
FIG. 2A provides a front side view of an embodiment of a medicament device.

FIG. 2A provides a front side view of an embodiment of a medicament device 300. A device housing 13a is provided to contain the various components of the medicament device embodiment 300. In the embodiment shown in FIG. 2A, the device housing 13a is reusable, however the housing can also be embodied as a single use housing. The device housing 13a in the embodiment of the medicament device 300 in FIG. 2A includes various components such as an actuation member 38, a safety mechanism 86, an indicator 80, a control interface 56 including a display 82, and responsive members 58. The device housing 13a further includes a number of sensors, for example, an orientation sensor 62, one or more contact sensors 64, a perpendicularity sensor 66, alignment sensor 70 or location sensor 72. The medicament device 300 further includes an audio output 78 associated with the device 300, an injection member 16 or injection simulation member 54, a memory module 74, circuitry 76 a microprocessor 68, and program code module 84 as described above.

FIG. 2B provides a cross-sectional view of an embodiment of a medicament device 300 as shown in FIG. 2A, however the container 11 can be seen inside of the device housing 13a. An identification information reader 50 and a unique identification information 48 are provided side by side. The first housing 10 and second housing 12 as well as the plunger 28 of the container 11 are provided in FIG. 2B within the device housing 13*a* of the medicament device 300.

Figure 3A:
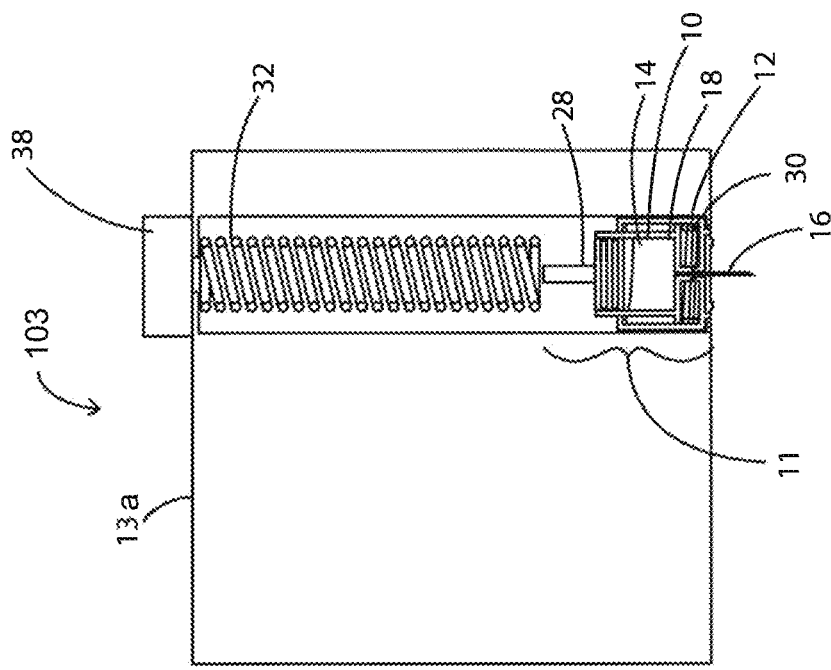
Figure 3B:
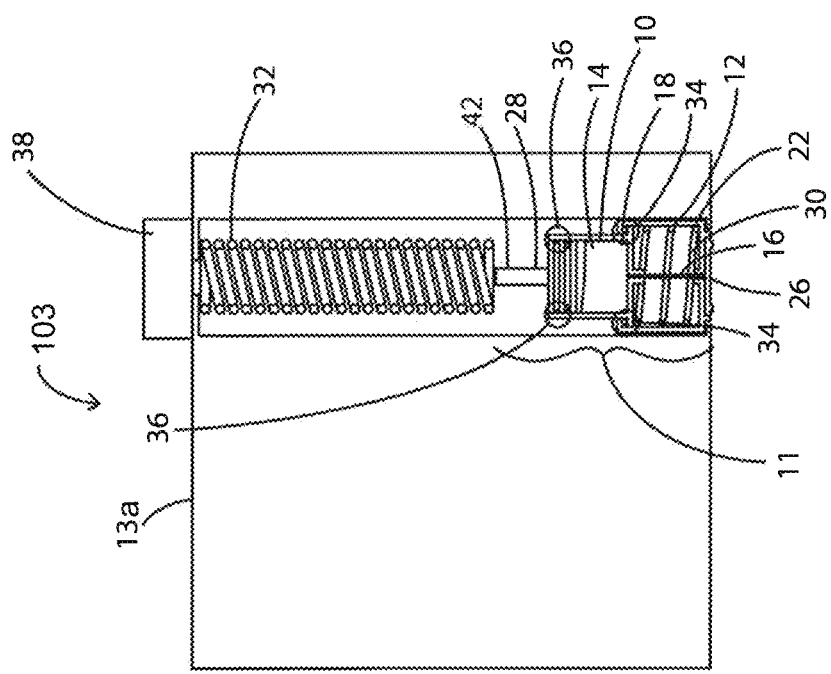

FIG. 3A-3D illustrate the steps of the user of an embodiment of the medicament delivery system 103. FIG. 3A provides the device housing 13*a* with the actuation member 38, a second spring associated therewith 32, associated with the first portion 42 of the plunger 28. The container 11 is shown with the second and third contaminant barriers in FIG. 3A. The third contaminant barrier 36 disposed between the plunger 28 and the first housing 10, and the second contaminant barrier 34 is shown as disposed between the first housing 10 and the second housing 12. The first spring 30 disposed between a lower portion of the first housing 18 and the lower portion of the second housing 22 is, in one example, a linear spring. The second spring 32 is also a linear spring, in one embodiment. Once the actuation member 38 is activated, as shown in FIG. 3B, the first spring 30 is compressed or biased as the first housing 10 moves relative to the second housing 12 in a first direction, whereby the injection member 16 traverses the first contaminant barrier 26 and enters or pierces the skin of a user in a delivery device. The first spring 30 will be biased or compressed before the second spring 32, in one embodiment, because the first spring 30 has a lesser resistance than the second spring 32. Insertion of a needle into the skin of a user requires less force than disbursement of a medicament through a needle into the skin of a user in most instances. Therefore, the system will take the path of least resistance and the first spring 30 will be biased or compressed before the second spring 32. In the a training device or training cartridge, where the injection simulation member 54 is in place of the injection member 16, the injection simulation member 54 upon activation of the actuation member 38 exits the first contaminant barrier 26 and abuts the skin of a user.

In FIG. 3C, the second spring 32 compresses the plunger 28 delivering the medicament 14 that was housed within the first housing 10 through the injection member 16 and into the skin of a user. Once the injection is complete, as illustrated in FIG. 3D, the first spring 30 is released, the first housing 10 moves in a second direction relative to the second housing 12, and the injection member 16 retracts back into the second housing 12 to protect the user from unintentionally sticking himself by contacting the injection member 16. In the embodiment in which the container 11 is removable and disposable, the container 11 can now be removed from the device housing 13*a* and safely disposed of.

FIG. 4 provides a device housing 13 according to an embodiment 300 of the invention. The device housing 13 is configured to receive a container 11. The container 11 can be screwed into the device housing in the embodiment illustrated in FIG. 4; however, one skilled in the art would appreciate that any type of fastening means known in the art can be used to connect the container 11 to the housing 13. FIG. 5A provides an embodiment of a container 11, which can be transported with a safety cap 88, so as to protect the container 11 and its contents (i.e., the medicament 14) from destruction or contaminants. Before connecting the container 11 to the device housing 13, the safety cap 88 is unscrewed from the container 11 (FIG. 5A) and the container is screwed onto the bottom of the device housing 13, in an embodiment (FIG. 5B-5C). Again, as mentioned above, the device housing 13 need not be reusable, and may be provided as a single-use housing in an embodiment.

Figures 5D, 5E, 5F, 5G:
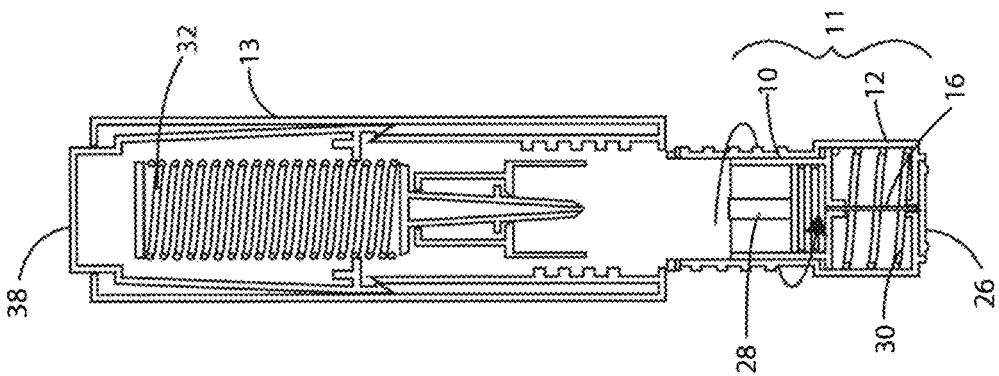

In FIG. 5D, the actuation member 38 is activated (for example by depressing the actuation member 38 toward the container 11), biasing the first spring 30. In FIG. 5D, the second spring 32 is biased, and the plunger 28 moves relative to the first housing 10 in a first direction to dispel the medicament 14 from the first housing 10 and deliver the medicament 14 through the injection member 16. After the injection is complete (FIG. 5F), the first spring 30 is released and the first housing 10 moves in a second direction relative to the second housing 12 so as to retract the injection member 16 into the second housing 12. The container 11 can then be removed from the device housing 13 as shown in FIG. 5G, and can be disposed of. Once the container 11 is removed from the housing 13, the locking mechanism is re-activated to prevent the first housing 10 from moving relative to the second housing 12 in a first direction, such that a user is protected from an unintentional sticking with the injection member 16 while handling the container 11 after use.

Also provided herein are various actuation mechanisms that can be implemented to move the components of the device. While some of the cam profiles provided in the Figures are single cam profiles, multiple cam profiles could be used on the barrel cam to act on the various components of the system, both single and multiple cam profiles are contemplated herein. Barrel cams are further described in the examples of the actuation mechanism below. Rotatable members such as the index cam described in more detail in reference to FIGS. 16A-D' are also examples of actuation mechanisms that can be implemented to move the components of the device relative to one another and initiate the functions of the device.

Various examples of injection simulation members 54 are provided herein. One skilled in the art would appreciate that the injection simulation members described herein may be used with the various container embodiments of the medicament device, including the single use and multi-use embodiments, as well as with the various non-container medicament device embodiments, such as the training embodiments described herein. One embodiment of an injection simulation member is illustrated as a flexible injection simulation member 54*a* in the cross sectional view of FIG. 6. Examples of flexible injection simulation members include injection simulation members including materials such as a resin with a high elastic memory, for example, a monofilament, in a non-limiting embodiment. The flexible injection simulation member 54*a* is configured to bend, flex, or change shape when it comes in contact with an object, such as a patient's skin, and will then return to its original shape and/or position once it is removed from the object or the patient's skin.

FIGS. 7A-7B provide a cross sectional view of a retractable injection simulation member 54*b* in an extended, activated position, wherein the injection simulation member 54*b* telescopes out into the activated position shown in FIG. 7A. The injection simulation member is shown in FIG. 7B in a retracted position. A spring 55 is shown in a biased state in FIG. 7A, wherein the injection simulation member 54*b* is telescoped from the container 11. The spring 55 shown is a tension spring in a compressed position in FIG. 7A and in an extended position in FIG. 7B. The retractable injection simulation member 54*b* allows a patient to practice an injection without puncturing his or her skin in the process, whereby the injection simulation member simulates the look and feel of an injection. Once the injection simulation member 54*b* comes in contact with the skin of the patient, the injection simulation member 54*b* will retract into the container 11. Once removed from the skin, the tension spring is compressed and the injection simulation member

54b is extended from the vial again. The force required for the injection simulation member to penetrate the skin is significantly higher than the spring load. As the path of the least resistance is sought by the actuation mechanism, the injection simulation member 54b will retract rather than eject into the skin.

FIG. 8 illustrates an injection simulation member 54c having a housing, wherein the housing for the injection simulation member 54c is provided for additional safety. In a non-limiting embodiment, the injection simulation member 54c is shown in FIG. 8 as having a resilient, transparent cover. Using this injection simulation member 54c, the patient can observe the properties of the injection simulation member 54c without risking an injury caused by a needle stick.

FIGS. 9A-9B provide another example of an injection simulation member 54d in which the member telescopes from a first position (FIG. 9B) wherein the injection simulation member 54d is retracted within the container 11 out into a second position (FIG. 9A), wherein the injection simulation member 54d is ejected from the container 11. In one embodiment, a spring 57 can be used to effect the movement of the injection simulation member 54d as shown in FIGS. 9A-9B. The embodiment shown in FIGS. 9A-9B provide a resilient transparent cover over the injection simulation member 54d.

FIGS. 10A-10H demonstrate a barrel cam actuation mechanism 90 as shown in the cross sectional view of FIG. 10A, for use with a multi-use injection device, wherein a container 11 including a medicament is joined with the injection device device housing 13 prior to an injection. The container 11 may include a safety cover 15 as shown in FIG. 10B, which can be removed from the container 11 prior to joining with the housing 13, wherein the housing includes the barrel cam actuation mechanism 90. The container 11 may include a series of nodules on a portion thereof, and the injection device may include a series of complementary nodules on a portion thereof, such that the container 11 can be adjoined to the device prior to injection as shown in FIG. 10C. The barrel cam actuation mechanism 90 includes a barrel 92, a cam groove 98, and a barrel actuation member 96, which can be configured as an actuation button, in a non-limiting example. A spring engagement member 112 and a plunger 114 associated with the barrel 92. The plunger 114 is configured to associate with the stopper 28 of the container 11. A ratcheting mechanism 97 is provided and can be activated so as to load the torsion spring 100. The housing 13 may include a cam pin 94 for engaging with the cam groove 98 on the barrel 92. In an alternative embodiment, the barrel 92 may include the cam pin 94 and the housing 13 may include the cam groove 98. The cam pin 94 is configured to engage with and move within the cam groove 98 on the barrel 92 as shown in FIGS. 10A and 10C-10H.

Once the container 11 is adjoined with the device housing 13, the barrel actuation member 96 is activated such that as the barrel 92 rotates within the housing 13, the cam pin 94 moves within the cam groove 98 profile, causing a linear displacement of the barrel 92 relative to the housing 13. As such, axial motion is converted into a linear motion. In one embodiment, the longitudinal axes of the barrel 92 and the housing 13 are co-linear. The linear motion is longitudinal to the axes of the housing 13 and the barrel 92. A first barrel cam spring 100 and second barrel cam spring 110 associated with the barrel cam mechanism 90, wherein the first barrel cam spring 100 is a torsion spring and the second barrel cam spring 110 is a compression spring in non-limiting embodiments and the second barrel cam spring 110 is associated with the spring engagement member 112. As a result of the actuation of the barrel actuation mechanism 90, rotational motion is transformed in to linear motion and the first housing 10 is moved relative to the second housing 12 in a first direction to eject the injection member 16 from the container 11, and thereafter the stopper moves relative to the first housing 10 to deliver medicament 14 through the injection member 16. Once an injection is complete, the container 11 may be removed from the housing 13 and discarded.

The barrel cam actuation mechanism 90 allows for varying speeds of the linear motion while the rotational motion may be at a constant speed. This property is derived through the shape of the cam profile of the cam groove 98. This infers precise speed control (timing) of the linear motion throughout the injection cycle. The barrel cam actuation mechanism 90 allows the start position to be the same as the end position by creating an infinite-loop cam profile. This property is desired for a repeat-use device, in one embodiment. The barrel cam actuation mechanism 90 can to be energized by multiple types of motivations, including electric motors and torsion springs, in non-limiting embodiments. The barrel cam provides a reliable actuation mechanism under many conditions. The barrel cam actuation mechanism 90 also provides for easy to establish failure mode test protocols, while providing a simple and low cost actuation mechanism which requires few parts. Because these actuation mechanisms are incorporated into a medical device, they must be extremely reliable. The barrel cam actuation mechanism 90 can be actuated at various speeds and effect injection at various speeds and accelerations. For example, in one embodiment it is preferred for the needle to be inserted into the skin quickly, but the stopper to traverse the first housing more slowly to minimize pain and increase therapeutic compliance. Furthermore, for auto injector embodiments, the cycle goes through multiple stages. For a reusable device, this cycle has to be reset to its original state once an injection is complete. At the end of the cycle, there must be a way to start again at the beginning of the cycle. The actuation mechanisms, in particular, the barrel actuation mechanism 90 described herein, provides a novel way of doing so.

FIG. 11 provides a schematic showing a cam profile of the cam groove 98 for one embodiment of the barrel cam actuation mechanism 90. The cam profile of FIG. 11 can be used with multi-use injection devices, for example. The cam profile allows for each phase of the injection and reset of the cycle of injection. The schematic of FIG. 11 is just a representation of the cam profile, as it is circumferentially oriented around the barrel 92 of the device.

As the barrel 92 rotates the cam pin 94 passes through following the cam groove 98 section through the following injection phases. Phase A is the start and finish position, here the barrel 92 is at rest, and the torsion spring 100 (in one embodiment) is loaded. This phase is shown in FIG. 10D. In B of FIG. 11, because of the straight vertical groove section, the barrel 92 has a sudden descent, assisted by the compression spring 110, and the first housing 10 of the container 11 moves into the second housing 12. This causes the injection member 16 to pierce through the membrane of the second housing 12, such that the injection member 16 ejects from the container 11 and can be inserted into a patient (this phase is shown in FIG. 10E).

Phase C shows the phase in which the injection member 16 is in the ejected position.

This cam groove 98 section causes the plunger 114 slowly to move into the first housing 10 and associate with the stopper 28, thereby expelling the medicament 14 through the injection member 16 (this stage is shown in 10F).

In phase D, after the medicament 14 is expelled through the injection member 16, it is often required that the injection member 16 stays in the tissue of the patient (e.g., subcutaneous tissue) for a period of time (4 seconds to 10 seconds, for example). This is the flat section—also called "dwell period"—of the cam profile. Although the barrel 92 continues to rotate, there is no injection member 16 motion, in an embodiment (this stage is shown in FIG. 10F).

In phase E, once the medicament is fully expelled from the first housing 10, the vial and injection member 16 retracts from the patient into the second housing 12 in this phase (this stage is shown in FIG. 10G). In phase F, the plunger 114 moves out of the first housing 10. As the container 11 is disposed with the stopper 28 inside the first housing, this step may only be necessary in a training device embodiment where all components have to be reset.

After phase F, the cam pin 94 seamlessly moves into the start/finish position of phase A, where it comes to a stop. At this point, after the torsion spring 100 is reloaded (FIG. 10H), the device is ready to be used again.

The barrel cam actuation mechanism 90 for use in a training device is demonstrated in FIGS. 12A-12E and FIG. 13. The cam profile for the cam groove 98 for the training injection device of FIG. 12 is substantially the same as that of FIG. 11. The training device of FIGS. 12A-E include an injection simulation member 54 in place of the injection member 16 of FIGS. 9A-H, and the plunger 114' having a different configuration than and in place of the plunger 114 of the previous embodiment. In place of the container 11, a single use training container 11' is provided within the housing 13' in the embodiment of FIGS. 12A-E. The training container may not include any medicament 14 as shown in the Figures herein. The injection simulation member 54 may include various embodiments as discussed herein. Reset of the barrel cam actuation mechanism 90 may reset the training aspect of the device in an embodiment.

Figure 13:
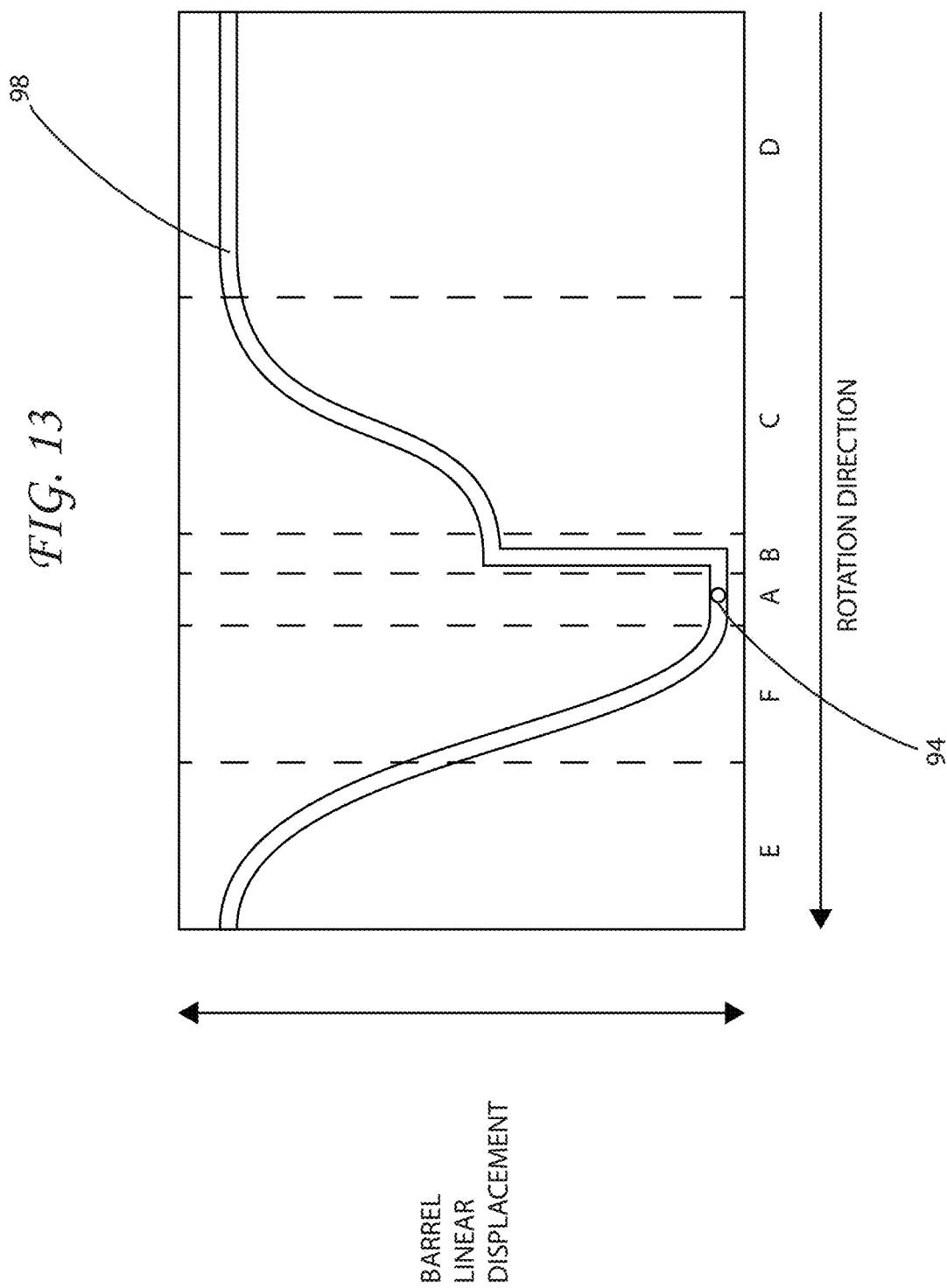
FIG. 13 provides a schematic illustration of a cam profile for a cam groove of the embodiment of FIGS. 12A-12E.

FIG. 13 shows phase A as the start and finish position, wherein the barrel 90 is at rest and the torsion spring 100 is loaded in an embodiment. This phase is also demonstrated in FIG. 11A.

In phase B, because of the straight vertical groove section, the barrel 90 has a sudden descent, assisted by the compression spring 110 in one embodiment. This phase is shown in FIG. 12B. In phase C, the injection simulation member 54 is in an ejected position. This groove section causes the plunger 114' to slowly to move into the vial or container 11'. This stage is shown in FIG. 12C. As represented in Phase D, and as aforementioned, it is often required in an actual injection, that the injection member stays in contact with the skin of the patient for a period of time (4 seconds to 10 seconds, for example). This is the flat section shown—also called "dwell period"—of the cam profile. Although the barrel 90 continues to rotate, there is no linear motion of the injection simulation member 54. This stage is shown in FIG. 12C. In phase E, after the dwell period (plunger 114' is fully in vial or container 11', the vial or container 11' with injection simulation member 54 retracts away from the skin, in one embodiment, into the housing of the device in this phase. This stage is shown in FIG. 12D. In phase F, the plunger 114' is removed from the vial or container 11'. After phase F, the cam pin 94 seamlessly moves into the start/finish position of Phase A, where it comes to a stop. At this point, after the torsion spring 100 is reloaded, in an embodiment the device is ready for the next training cycle.

In yet a further embodiment, the barrel cam actuation mechanism 90 is shown in FIGS. 14A-D, and FIG. 15 for use with a single dose injection device. No ratcheting mechanism is necessary in the embodiment of FIGS. 14A-D, as the torsion spring 100 will be pre-loaded, in an embodiment. As in the embodiments already described herein, a torsion spring 100 can be used to motivate axial rotation of the barrel 92, and a compression spring 110 can facilitate acceleration of the container 11" which includes the injection member 16 and is disposed within the device housing 13', and the medicament 14, wherein the container 11" is associated with the plunger 114" which includes a stopper 28' at its distal end which is in fluid communication with the medicament 14 in the container 11".

FIG. 15 shows an embodiment of a cam profile for the cam groove 98 of the embodiment of the device shown in FIGS. 14A-D. Phase A shows the start position of the injection, wherein the barrel 92 is at rest and the torsion spring 100, in this embodiment, is loaded. This phase is shown in FIG. 14A. In phase B, where the straight vertical groove section of the cam groove 98 is represented, the barrel 92 has a sudden descent, assisted by the compression spring 110, in one embodiment. The injection member 16 penetrates the skin of a patient (i.e., into the subcutaneous tissue). This phase is shown in FIG. 14B. In phase C, the injection member 16 is in the skin of the patient, and this groove section causes the plunger 114" to slowly move into the vial or container", thereby expelling the medicament 14 through the injection member 16. This stage is shown in FIG. 14C.

As shown in phase D, it is often required that the injection member 16 stays in the patient for a period of time (4 seconds to 10 seconds, for example). This is represented by the flat section of the groove—also called "dwell period"— of the cam profile. Although the barrel 92 continues to rotate, there is no linear motion of the injection member 16. This stage is shown in FIG. 14C. In phase E, after the dwell period (container eng is fully in vial), the vial with the plunger fully inside retracts and the injection member is removed from the patient. This stage is shown in FIG. 14D. After phase E, the barrel 92 comes to a stop, and at this point, the device can be disposed.

FIGS. 16A-16D' illustrate an embodiment of the device and system wherein the actuation mechanism 91 is a rotational member. In one non-limiting example, the rotational member can be an index cam. The actuation mechanism 91 includes a first threaded portion 46 and a second threaded portion 44, in one embodiment, provided to integrate with and provide movement of the various components of the container 11 to execute an injection or a simulated injection. In the Figures provided, the rotatable actuation mechanism 91 includes two threaded portions; however, one skilled in the art would appreciate that the same could be accomplished with only one threaded portion or with more than two threaded portions on the rotatable member 91. In the Figures shown herein, the rotational member is associated with a motor 154 provided, in an embodiment, to power or activate the rotational member or actuation mechanism 91.

FIG. 16A provides a top end view of a rotatable actuation mechanism 91 and a container 11 in a first position. Once the rotatable actuation mechanism 91 is activated, it is rotated in a first direction such that the second threaded portion 44, which interacts with a projection member 40 on the first housing 10 of the container 11 is moved in a first direction relative to the second housing 12 to bias the spring 30 and extend the injection member 16 through the first contaminant barrier 26 as demonstrated in FIGS. 16B and 16B'. As the rotatable actuation mechanism 91 continues its rotation in the first direction, a first threaded portion 46 comes in contact with the plunger component 28 and by continued rotation of the rotatable actuation mechanism 91 the plunger component 28 is moved in a first direction relative to the first housing 10 to deliver the medicament 14 through the injection member 16 and into the skin of a user as seen in FIGS. 16C and 16C'. FIGS. 16C-16D show an opening 52 in the second threaded portion 44 whereby the projection member 40 is released to release the spring 30 such that the first housing 10 moves in a second direction relative to the second housing 12 so as to retract the injection member 16 into the second housing 12. In an embodiment, the unique identification information 48 is provided on the container 11, as can be seen in FIGS. 16A-16D' and the identification information reader 50 is provided on the actuation mechanism 91 as is shown in FIGS. 16C'-16D'.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the preceding definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, any means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A system for storing and delivering an injection member and a medicament in a sterile condition until injection, the system comprising:
    a reusable housing comprising a receptacle for receiving a container to be housed there within, the reusable housing comprising an actuation mechanism;
    a container removably receivable within the receptacle, the container comprising
        a first housing containing a sterile medicament, said first housing preventing contamination of the medicament contained there within;
        a second housing, wherein the first housing is movable relative to the second housing;
        an injection member associated with a lower portion of the first housing;
        a stopper associated with the first housing, wherein a movement of the stopper in a first direction first causes movement of the first housing relative to the second housing in a first direction to deliver the injection member, and subsequent movement of the stopper relative to the first housing to deliver the medicament through the injection member;
        a first contaminant barrier disposed at a lower portion of the second housing;
        a second contaminant barrier disposed between the second housing and the first housing to maintain sterility of the second housing, such that the first contaminant barrier, the second contaminant barrier, and the second housing are configured to seal the second housing to maintain sterility of the injection member until injection, and to prevent contact with the injection member prior to the injection and post injection; and
        a spring disposed between the first and second housings such that when the first housing moves relative to the second housing in a first direction to deliver the medicament, the spring is biased, and the injection member extends from the second housing traversing the first contaminant barrier, and after the medicament is delivered through the injection member the spring is released, the first housing moves relative to the second housing in a second direction, and the injection member is retracted into the second housing to prevent unintentional contact with the injection member;
    wherein sterility of the injection member is maintained from prior to insertion of the container into the reusable housing through traversal of the injection member through the first contaminant barrier, sterility of the medicament is maintained until the medicament is delivered through the injection member, and actuation of the system occurs by movement of the stopper in the first direction.

2. The container of claim 1, wherein the injection member traverses the first contaminant barrier and the stopper is depressed so as to deliver the medicament through the injection member.

3. The container of claim 1, wherein the stopper is associated with a shaft.

4. The container of claim 1, wherein the stopper is associated with a third contaminant barrier.

5. The container of claim 4, wherein the third contaminant barrier prevents contaminants from entering the first housing and/or the medicament.

6. The container of claim 1, wherein the container does not comprise an actuation mechanism.

7. A medicament delivery or injection simulation system, comprising:
    a reusable housing comprising an actuation mechanism and a receptacle for receiving a container to be housed there within,
    a container being removably receivable within the receptacle, the container comprising a first housing and a second housing, wherein the first housing comprises a sterile medicament and is movable relative to the second housing, upon initiation of the actuation mechanism, the second housing comprising a first contaminant barrier at a lower portion thereof;

a second contaminant barrier disposed between an upper portion of the second housing and a lower portion of the first housing to maintain sterility of the second housing until injection;

an injection member or an injection simulation member associated with a lower portion of the first housing; and a stopper associated with the first housing, wherein actuation of the system occurs by movement of the stopper in a first direction relative to the container, said movement of the stopper first moves the first housing relative to the second housing in a first direction to extend the injection member or injection simulation member from the second housing traversing the first contaminant barrier, and subsequent movement of the stopper relative to the first housing to deliver medicament through the injection member;

following delivery of medicament, the first housing moves relative to the second housing in a second direction the injection member or injection simulation member is retracted into the second housing to prevent an unintentional contact with the injection member or injection simulation member, wherein sterility of the injection member or injection simulation member is maintained from prior to insertion of the container into the reusable housing through traversal of the injection member through the first contaminant barrier, and sterility of the medicament is maintained until the medicament is delivered.

8. The medicament delivery or injection simulation system of claim 7, wherein the actuation mechanism comprises a motor.

9. The medicament delivery or injection simulation system of claim 7, wherein the actuation mechanism comprises a motor that drives the movement of the stopper.

10. The medicament delivery or injection simulation system of claim 7, wherein a third contaminant barrier is disposed between the stopper and the first housing to prevent contaminants from entering the first housing and/or the medicament.

11. The medicament delivery or injection simulation system of claim 7, further comprising a shaft connected to said stopper.

12. A system for delivering a medicament, the system comprising:

a reusable housing comprising a receptacle for receiving a container to be housed there within, the reusable housing comprising an actuation mechanism;

a container removably receivable within the receptacle, the container for storing the medicament until injection, the container comprising a first housing comprising a medicament, the first housing comprising a flange at a lower portion thereof;

a second housing, wherein the first housing is movable relative to the second housing, the second housing comprising a shoulder at an upper portion thereof;

an injection member associated with a lower portion of the first housing;

a plunger associated with the first housing, said plunger being movable relative to the first housing;

a first contaminant barrier disposed at a lower portion of the second housing; and a second contaminant barrier between the shoulder and the flange, the second housing, second contaminant barrier, first contaminant barrier and the first housing to maintain sterility of the injection member and prevent contaminants from entering the second housing prior to insertion of the container into the reusable housing until extension of the injection member from the housing;

wherein upon actuation of the actuation mechanism, the first housing moves relative to the second housing in a first direction, the injection member extends from the second housing traversing the first contaminant barrier, and the plunger moves relative to the first housing in a first direction to deliver the medicament through the injection member, wherein the sterility of the medicament and the injection member are maintained from prior to insertion of the container into the reusable housing through delivery of the medicament, and the injection member, respectively, wherein movement of the first housing relative to the second housing in a second direction retracts the injection member into the second housing to prevent an unintentional contact with the injection member.

* * * * *